(12) United States Patent
Losordo et al.

(10) Patent No.: US 9,943,427 B2
(45) Date of Patent: Apr. 17, 2018

(54) SHAPED OCCLUDING DEVICES AND METHODS OF USING THE SAME

(71) Applicant: Covidien LP, Mansfield, MA (US)

(72) Inventors: Michael Louis Losordo, San Juan Capistrano, CA (US); Masoud Molaei, Mountain View, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/669,944

(22) Filed: Nov. 6, 2012

(65) Prior Publication Data
US 2014/0128957 A1 May 8, 2014

(51) Int. Cl.
| | | |
|---|---|---|
| *A61F 2/90* | (2013.01) | |
| *A61F 2/82* | (2013.01) | |
| *A61F 2/06* | (2013.01) | |

(52) U.S. Cl.
CPC .......... *A61F 2/90* (2013.01); *A61F 2002/068* (2013.01); *A61F 2002/823* (2013.01); *A61F 2230/008* (2013.01)

(58) Field of Classification Search
USPC .......... 623/1.2, 1.3–1.31, 1.34, 1.53
See application file for complete search history.

(56) References Cited

U.S. PATENT DOCUMENTS

| | | |
|---|---|---|
| 2,919,467 A | 1/1960 | Mercer |
| 4,321,711 A | 3/1982 | Mano |
| 4,503,569 A | 3/1985 | Dotter |
| 4,512,338 A | 4/1985 | Balko et al. |
| 4,538,622 A | 9/1985 | Samson et al. |
| 4,572,186 A | 2/1986 | Gould et al. |

(Continued)

FOREIGN PATENT DOCUMENTS

| | | |
|---|---|---|
| CN | 101472537 A | 7/2009 |
| EP | 855170 | 7/1998 |

(Continued)

OTHER PUBLICATIONS

Benndorf, et al. Treatment of a Ruptured Dissecting Vertebral Artery Aneurysm with Double Stent Placement: Case Report AJNR Am J Neuroradiol, Nov.-Dec. 2001, vol. 22, pp. 1844-1848.

(Continued)

*Primary Examiner* — Leslie Lopez
(74) *Attorney, Agent, or Firm* — Fortem IP LLP; Matthew Lincicum

(57) ABSTRACT

A self-expanding stent includes a proximal portion having a first cross-sectional area in an expanded state, a distal portion having a second cross-sectional area in an expanded state, a narrowed portion between the proximal portion and the distal portion, the narrowed portion comprising a cross-sectional area when in an expanded state that is less than the first cross-sectional area and the second cross-sectional area, wherein the narrowed portion is configured to increases flow velocity in the narrowed portion while reducing reduce pressure against a distal wall of the aneurysm by being axially disposed substantially between a proximal edge and a distal edge of an aneurysm neck or ostium, the flow traversing through the lumen of the self-expanding stent. In use, the self-expanding stent is positioned at the site of an aneurysm and expanded via release from a stent delivery device.

21 Claims, 4 Drawing Sheets

(56) References Cited

U.S. PATENT DOCUMENTS

| | | | |
|---|---|---|---|
| 4,580,568 A | 4/1986 | Gianturco | |
| 4,655,771 A | 4/1987 | Wallsten | |
| 4,681,110 A | 7/1987 | Wiktor | |
| 4,733,665 A | 3/1988 | Palmaz | |
| 4,743,251 A | 5/1988 | Barra | |
| 4,768,507 A | 9/1988 | Fischell et al. | |
| 4,776,337 A | 10/1988 | Palmaz | |
| 4,856,516 A | 8/1989 | Hillstead | |
| 4,954,126 A | 9/1990 | Wallsten | |
| 5,011,488 A | 4/1991 | Ginsburg | |
| 5,035,706 A | 7/1991 | Giantureo et al. | |
| 5,041,126 A | 8/1991 | Gianturco | |
| 5,061,275 A | 10/1991 | Wallsten et al. | |
| 5,108,416 A | 4/1992 | Ryan et al. | |
| 5,160,341 A | 11/1992 | Brenneman et al. | |
| 5,180,368 A | 1/1993 | Garrison | |
| 5,192,297 A | 3/1993 | Hull | |
| 5,197,978 A | 3/1993 | Hess | |
| 5,201,757 A | 4/1993 | Heyn et al. | |
| 5,209,731 A | 5/1993 | Sterman et al. | |
| 5,242,399 A | 9/1993 | Lau et al. | |
| 5,246,420 A | 9/1993 | Kraus et al. | |
| 5,246,445 A | 9/1993 | Yachia et al. | |
| 5,330,500 A | 7/1994 | Song | |
| 5,344,426 A | 9/1994 | Lau et al. | |
| 5,360,443 A | 11/1994 | Barone et al. | |
| 5,366,504 A * | 11/1994 | Andersen | A61F 2/04 606/194 |
| 5,382,259 A | 1/1995 | Phelps et al. | |
| 5,401,257 A | 3/1995 | Chevalier, Jr. et al. | |
| 5,405,377 A | 4/1995 | Cragg | |
| 5,405,380 A | 4/1995 | Gianotti et al. | |
| 5,415,637 A | 5/1995 | Khosravi | |
| 5,421,826 A | 6/1995 | Crocker et al. | |
| 5,423,849 A | 6/1995 | Engelson et al. | |
| 5,449,372 A | 9/1995 | Schmaltz et al. | |
| 5,458,615 A | 10/1995 | Klemm et al. | |
| 5,476,505 A | 12/1995 | Limon | |
| 5,480,423 A | 1/1996 | Ravenscroft et al. | |
| 5,484,444 A | 1/1996 | Braunschweiler et al. | |
| 5,489,295 A | 2/1996 | Piplani et al. | |
| 5,507,767 A | 4/1996 | Maeda et al. | |
| 5,507,768 A | 4/1996 | Lau et al. | |
| 5,522,822 A | 6/1996 | Phelps et al. | |
| 5,534,007 A | 7/1996 | St. Germain et al. | |
| 5,545,208 A | 8/1996 | Wolff et al. | |
| 5,546,880 A | 8/1996 | Ronyak et al. | |
| 5,549,662 A | 8/1996 | Fordenbacher | |
| 5,562,641 A | 10/1996 | Flomenblit et al. | |
| 5,562,728 A | 10/1996 | Lazarus et al. | |
| 5,591,225 A | 1/1997 | Okuda | |
| 5,599,291 A | 2/1997 | Balbierz et al. | |
| 5,601,593 A | 2/1997 | Freitag | |
| 5,607,466 A | 3/1997 | Imbert et al. | |
| 5,609,625 A | 3/1997 | Piplani et al. | |
| 5,626,602 A | 5/1997 | Gianotti et al. | |
| 5,628,783 A | 5/1997 | Quiachon et al. | |
| 5,628,788 A | 5/1997 | Pinchuk | |
| 5,632,771 A | 5/1997 | Boatman et al. | |
| 5,632,772 A | 5/1997 | Alcime et al. | |
| 5,636,641 A | 6/1997 | Fariabi | |
| 5,637,113 A | 6/1997 | Tartaglia et al. | |
| 5,639,278 A | 6/1997 | Dereume et al. | |
| 5,645,559 A * | 7/1997 | Hachtman et al. | 623/1.2 |
| D381,932 S | 8/1997 | Walshe et al. | |
| 5,667,522 A | 9/1997 | Flomenblit et al. | |
| 5,674,276 A | 10/1997 | Andersen et al. | |
| 5,683,451 A | 11/1997 | Lenker et al. | |
| 5,690,120 A | 11/1997 | Jacobsen et al. | |
| 5,690,644 A | 11/1997 | Yurek et al. | |
| 5,695,499 A | 12/1997 | Helgerson et al. | |
| 5,700,269 A | 12/1997 | Pinchuk et al. | |
| 5,702,418 A | 12/1997 | Ravenscroft | |
| 5,709,702 A | 1/1998 | Cogita | |
| 5,709,703 A | 1/1998 | Lukic et al. | |
| 5,718,159 A | 2/1998 | Thompson | |
| 5,725,570 A | 3/1998 | Heath | |
| 5,733,327 A | 3/1998 | Igaki et al. | |
| 5,735,859 A | 4/1998 | Fischell et al. | |
| 5,741,325 A * | 4/1998 | Chaikof et al. | 623/1.35 |
| 5,741,333 A * | 4/1998 | Frid | 623/1.2 |
| 5,746,765 A | 5/1998 | Kleshinski et al. | |
| 5,749,883 A | 5/1998 | Halpern | |
| 5,749,920 A | 5/1998 | Quiachon et al. | |
| 5,769,884 A | 6/1998 | Solovay | |
| 5,769,885 A | 6/1998 | Quiachon et al. | |
| 5,776,099 A | 7/1998 | Tremulis | |
| 5,776,142 A | 7/1998 | Gunderson | |
| 5,782,909 A | 7/1998 | Quiachon et al. | |
| 5,797,952 A | 8/1998 | Klein | |
| 5,800,518 A | 9/1998 | Piplani et al. | |
| 5,810,837 A | 9/1998 | Hofmann et al. | |
| 5,817,102 A | 10/1998 | Johnson et al. | |
| 5,817,105 A | 10/1998 | Van Der Brug | |
| 5,824,039 A | 10/1998 | Piplani et al. | |
| 5,824,041 A | 10/1998 | Lenker et al. | |
| 5,824,042 A | 10/1998 | Lombardi et al. | |
| 5,824,044 A | 10/1998 | Quiachon et al. | |
| 5,824,058 A | 10/1998 | Ravenscroft et al. | |
| 5,830,229 A | 11/1998 | Konya et al. | |
| 5,833,632 A | 11/1998 | Jacobsen et al. | |
| 5,836,868 A | 11/1998 | Ressemann et al. | |
| 5,843,168 A | 12/1998 | Dang | |
| 5,868,754 A | 2/1999 | Levine et al. | |
| 5,876,419 A | 3/1999 | Carpenter et al. | |
| 5,876,445 A * | 3/1999 | Andersen | A61F 2/90 623/23.7 |
| 5,888,201 A | 3/1999 | Stinson et al. | |
| 5,902,266 A | 5/1999 | Leone et al. | |
| 5,902,317 A | 5/1999 | Kleshinski et al. | |
| 5,906,640 A | 5/1999 | Penn et al. | |
| 5,911,717 A | 6/1999 | Jacobsen et al. | |
| 5,916,194 A | 6/1999 | Jacobsen et al. | |
| 5,919,204 A | 7/1999 | Lukic et al. | |
| 5,928,260 A | 7/1999 | Chin et al. | |
| 5,944,728 A | 8/1999 | Bates | |
| 5,951,599 A | 9/1999 | McCrory | |
| 5,957,973 A | 9/1999 | Quiachon et al. | |
| 5,957,974 A | 9/1999 | Thompson et al. | |
| 5,964,797 A | 10/1999 | Ho | |
| 5,980,530 A | 11/1999 | Willard et al. | |
| 5,980,533 A | 11/1999 | Holman | |
| 5,984,957 A | 11/1999 | Laptewicz, Jr. et al. | |
| 6,012,277 A | 1/2000 | Prins et al. | |
| 6,014,919 A | 1/2000 | Jacobsen et al. | |
| 6,015,432 A | 1/2000 | Rakos et al. | |
| 6,017,319 A | 1/2000 | Jacobsen et al. | |
| 6,019,778 A | 2/2000 | Wilson et al. | |
| 6,019,786 A | 2/2000 | Thompson | |
| 6,022,369 A | 2/2000 | Jacobsen et al. | |
| 6,024,754 A | 2/2000 | Engelson | |
| 6,024,763 A | 2/2000 | Lenker et al. | |
| 6,027,516 A | 2/2000 | Kolobow et al. | |
| 6,033,436 A | 3/2000 | Steinke et al. | |
| 6,039,721 A | 3/2000 | Johnson et al. | |
| 6,039,758 A | 3/2000 | Quiachon et al. | |
| 6,042,589 A | 3/2000 | Marianne | |
| 6,051,021 A | 4/2000 | Frid | |
| 6,056,993 A | 5/2000 | Leidner et al. | |
| 6,063,111 A | 5/2000 | Hieshima et al. | |
| 6,074,407 A | 6/2000 | Levine et al. | |
| 6,077,295 A | 6/2000 | Limon et al. | |
| 6,080,191 A | 6/2000 | Summers | |
| 6,083,257 A | 7/2000 | Taylor et al. | |
| 6,093,199 A | 7/2000 | Brown et al. | |
| 6,096,052 A | 8/2000 | Callister et al. | |
| 6,102,942 A | 8/2000 | Ahari | |
| 6,123,712 A | 9/2000 | Di Caprio et al. | |
| 6,126,685 A | 10/2000 | Lenker et al. | |
| 6,132,459 A | 10/2000 | Piplani et al. | |
| 6,139,543 A | 10/2000 | Esch et al. | |
| 6,146,415 A | 11/2000 | Fitz | |
| 6,149,680 A | 11/2000 | Shelso et al. | |
| 6,159,228 A | 12/2000 | Frid et al. | |

(56) References Cited

U.S. PATENT DOCUMENTS

| | | |
|---|---|---|
| 6,161,399 A | 12/2000 | Jayaraman |
| 6,165,194 A | 12/2000 | Denardo |
| 6,165,210 A | 12/2000 | Lau et al. |
| 6,165,213 A | 12/2000 | Goicoechea et al. |
| 6,168,592 B1 | 1/2001 | Kupiecki et al. |
| 6,174,330 B1 | 1/2001 | Stinson |
| 6,183,410 B1 | 2/2001 | Jacobsen et al. |
| 6,183,508 B1 | 2/2001 | Stinson et al. |
| 6,187,013 B1 | 2/2001 | Stoltze |
| 6,193,708 B1 | 2/2001 | Ken et al. |
| 6,197,046 B1 | 3/2001 | Piplani et al. |
| 6,203,569 B1 | 3/2001 | Wijay |
| 6,206,868 B1 | 3/2001 | Parodi |
| 6,210,400 B1 | 4/2001 | Hebert et al. |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,214,042 B1 | 4/2001 | Jacobsen et al. |
| 6,221,102 B1 | 4/2001 | Baker et al. |
| 6,224,609 B1 | 5/2001 | Ressemann et al. |
| 6,224,829 B1 | 5/2001 | Piplani et al. |
| 6,231,598 B1 | 5/2001 | Berry et al. |
| 6,235,050 B1 | 5/2001 | Quiachon et al. |
| 6,241,759 B1 | 6/2001 | Piplani et al. |
| 6,245,087 B1 | 6/2001 | Addis |
| 6,245,103 B1 | 6/2001 | Stinson |
| 6,251,132 B1 | 6/2001 | Ravenscroft et al. |
| 6,258,115 B1 | 7/2001 | Dubrul |
| 6,260,458 B1 | 7/2001 | Jacobsen et al. |
| 6,261,305 B1 | 7/2001 | Marotta et al. |
| 6,261,316 B1 | 7/2001 | Shaolian et al. |
| 6,264,671 B1 | 7/2001 | Stack et al. |
| 6,264,689 B1 | 7/2001 | Colgan et al. |
| 6,270,523 B1 | 8/2001 | Herweck et al. |
| 6,280,465 B1 | 8/2001 | Cryer |
| 6,283,991 B1 | 9/2001 | Cox et al. |
| 6,287,331 B1 | 9/2001 | Heath |
| 6,287,333 B1 | 9/2001 | Appling et al. |
| 6,290,721 B1 | 9/2001 | Heath |
| 6,299,636 B1 | 10/2001 | Schmitt et al. |
| 6,302,810 B2 | 10/2001 | Yokota |
| 6,302,893 B1 | 10/2001 | Limon et al. |
| 6,309,353 B1 | 10/2001 | Cheng et al. |
| 6,322,576 B1 | 11/2001 | Wallace et al. |
| 6,322,586 B1 | 11/2001 | Monroe et al. |
| 6,322,587 B1 | 11/2001 | Quiachon et al. |
| 6,325,826 B1 | 12/2001 | Vardi et al. |
| 6,334,871 B1 | 1/2002 | Dor et al. |
| 6,336,938 B1 | 1/2002 | Kavteladze et al. |
| 6,340,367 B1 | 1/2002 | Stinson et al. |
| 6,340,368 B1 | 1/2002 | Verbeck |
| 6,342,068 B1 | 1/2002 | Thompson |
| 6,344,041 B1 | 2/2002 | Kupiecki et al. |
| 6,348,063 B1 | 2/2002 | Yassour et al. |
| 6,350,199 B1 | 2/2002 | Williams et al. |
| 6,350,278 B1 | 2/2002 | Lenker et al. |
| 6,355,051 B1 | 3/2002 | Sisskind et al. |
| 6,355,061 B1 | 3/2002 | Quiachon et al. |
| 6,364,895 B1 | 4/2002 | Greenhalgh |
| 6,368,339 B1 * | 4/2002 | Amplatz ............ A61B 17/0057 606/200 |
| 6,368,344 B1 | 4/2002 | Fitz |
| 6,368,557 B1 | 4/2002 | Piplani et al. |
| 6,375,670 B1 | 4/2002 | Greenhalgh |
| 6,375,676 B1 | 4/2002 | Cox |
| 6,379,618 B1 | 4/2002 | Piplani et al. |
| 6,380,457 B1 | 4/2002 | Yurek et al. |
| 6,389,946 B1 | 5/2002 | Frid |
| 6,395,017 B1 | 5/2002 | Dwyer et al. |
| 6,395,021 B1 | 5/2002 | Hart et al. |
| 6,395,022 B1 | 5/2002 | Piplani et al. |
| 6,398,802 B1 | 6/2002 | Yee |
| 6,409,683 B1 | 6/2002 | Fonseca et al. |
| 6,413,235 B1 | 7/2002 | Parodi |
| 6,416,519 B1 | 7/2002 | VanDusseldorp |
| 6,416,536 B1 | 7/2002 | Yee |
| 6,419,693 B1 | 7/2002 | Fariabi |
| 6,428,489 B1 | 8/2002 | Jacobsen et al. |
| 6,440,088 B1 | 8/2002 | Jacobsen et al. |
| 6,443,971 B1 | 9/2002 | Boylan et al. |
| 6,443,979 B1 | 9/2002 | Stalker et al. |
| 6,454,999 B1 | 9/2002 | Farhangnia et al. |
| 6,468,301 B1 | 10/2002 | Amplatz et al. |
| 6,477,768 B1 | 11/2002 | Wildner |
| 6,478,778 B1 | 11/2002 | Jacobsen et al. |
| 6,482,221 B1 | 11/2002 | Hebert et al. |
| 6,488,705 B2 | 12/2002 | Schmitt et al. |
| 6,491,648 B1 | 12/2002 | Cornish et al. |
| 6,494,895 B2 | 12/2002 | Addis |
| 6,497,711 B1 | 12/2002 | Plaia et al. |
| 6,503,450 B1 | 1/2003 | Afzal et al. |
| 6,514,261 B1 | 2/2003 | Randall et al. |
| 6,514,285 B1 | 2/2003 | Pinchasik |
| 6,524,299 B1 | 2/2003 | Tran et al. |
| 6,527,763 B2 | 3/2003 | Esch et al. |
| 6,533,811 B1 | 3/2003 | Ryan et al. |
| 6,540,778 B1 | 4/2003 | Quiachon et al. |
| 6,547,779 B2 | 4/2003 | Levine et al. |
| 6,551,352 B2 | 4/2003 | Clerc et al. |
| 6,572,646 B1 | 6/2003 | Boylan et al. |
| 6,576,006 B2 | 6/2003 | Limon et al. |
| 6,582,460 B1 | 6/2003 | Cryer |
| 6,582,461 B1 | 6/2003 | Burmeister et al. |
| 6,589,273 B1 | 7/2003 | McDermott |
| 6,592,616 B1 | 7/2003 | Stack et al. |
| 6,595,989 B1 | 7/2003 | Schaer |
| 6,602,271 B2 | 8/2003 | Adams et al. |
| 6,602,280 B2 | 8/2003 | Chobotov |
| 6,605,110 B2 | 8/2003 | Harrison |
| 6,613,075 B1 | 9/2003 | Healy et al. |
| 6,613,078 B1 | 9/2003 | Barone |
| 6,622,604 B1 | 9/2003 | Chouinard et al. |
| 6,623,518 B2 | 9/2003 | Thompson et al. |
| 6,635,068 B1 | 10/2003 | Dubrul et al. |
| 6,638,243 B2 | 10/2003 | Kupiecki |
| 6,645,240 B2 | 11/2003 | Yee |
| 6,646,218 B1 | 11/2003 | Campbell et al. |
| 6,652,508 B2 | 11/2003 | Griffin et al. |
| 6,652,574 B1 | 11/2003 | Jayaraman |
| 6,656,212 B2 | 12/2003 | Ravenscroft et al. |
| 6,656,218 B1 | 12/2003 | Denardo et al. |
| 6,660,024 B1 | 12/2003 | Flaherty et al. |
| 6,660,032 B2 | 12/2003 | Klumb et al. |
| 6,663,666 B1 | 12/2003 | Quiachon et al. |
| 6,666,881 B1 | 12/2003 | Richter et al. |
| 6,669,719 B2 | 12/2003 | Wallace et al. |
| 6,673,089 B1 | 1/2004 | Yassour et al. |
| 6,673,100 B2 | 1/2004 | Diaz et al. |
| 6,679,893 B1 | 1/2004 | Tran |
| 6,682,557 B1 | 1/2004 | Quiachon et al. |
| 6,685,735 B1 | 2/2004 | Ahari |
| 6,689,120 B1 | 2/2004 | Gerdts |
| 6,689,162 B1 | 2/2004 | Thompson |
| 6,699,274 B2 | 3/2004 | Stinson |
| 6,702,843 B1 | 3/2004 | Brown et al. |
| 6,709,454 B1 | 3/2004 | Cox et al. |
| 6,712,834 B2 | 3/2004 | Yassour et al. |
| 6,726,700 B1 | 4/2004 | Levine |
| 6,733,519 B2 | 5/2004 | Lashinski et al. |
| 6,740,105 B2 | 5/2004 | Yodfat et al. |
| 6,740,112 B2 | 5/2004 | Yodfat et al. |
| 6,743,219 B1 | 6/2004 | Dwyer et al. |
| 6,755,855 B2 | 6/2004 | Yurek et al. |
| 6,758,885 B2 | 7/2004 | Leffel et al. |
| 6,767,361 B2 | 7/2004 | Quiachon et al. |
| 6,773,446 B1 | 8/2004 | Dwyer et al. |
| 6,793,667 B2 | 9/2004 | Hebert et al. |
| 6,814,746 B2 | 11/2004 | Thompson et al. |
| 6,814,748 B1 | 11/2004 | Baker et al. |
| 6,818,006 B2 | 11/2004 | Douk et al. |
| 6,833,003 B2 | 12/2004 | Jones et al. |
| 6,849,084 B2 | 2/2005 | Rabkin et al. |
| 6,858,034 B1 | 2/2005 | Hijlkema et al. |
| 6,860,893 B2 | 3/2005 | Wallace et al. |

(56) References Cited

U.S. PATENT DOCUMENTS

| | | |
|---|---|---|
| 6,860,898 B2 | 3/2005 | Stack et al. |
| 6,860,899 B1 | 3/2005 | Rivelli, Jr. |
| 6,860,900 B2 | 3/2005 | Clerc et al. |
| 6,860,901 B1 | 3/2005 | Baker et al. |
| 6,866,677 B2 | 3/2005 | Douk et al. |
| 6,866,679 B2 | 3/2005 | Kusleika |
| 6,866,680 B2 | 3/2005 | Yassour et al. |
| 6,881,221 B2 | 4/2005 | Golds |
| 6,887,267 B2 | 5/2005 | Dworschak et al. |
| 6,890,337 B2 | 5/2005 | Feeser et al. |
| 6,893,451 B2 | 5/2005 | Cano et al. |
| 6,918,921 B2 | 7/2005 | Brady et al. |
| 6,932,837 B2 | 8/2005 | Amplatz et al. |
| 6,936,055 B1 | 8/2005 | Ken et al. |
| 6,955,685 B2 | 10/2005 | Escamilla et al. |
| 6,960,227 B2 | 11/2005 | Jones et al. |
| 6,964,670 B1 | 11/2005 | Shah et al. |
| 6,964,672 B2 | 11/2005 | Brady et al. |
| 6,969,396 B2 | 11/2005 | Krolik et al. |
| 6,976,991 B2 | 12/2005 | Hebert et al. |
| 6,989,024 B2 | 1/2006 | Hebert et al. |
| 6,994,721 B2 | 2/2006 | Israel |
| 7,001,422 B2 | 2/2006 | Escamilla et al. |
| 7,004,962 B2 | 2/2006 | Stinson |
| 7,004,964 B2 | 2/2006 | Thompson et al. |
| 7,011,675 B2 | 3/2006 | Hemerick et al. |
| 7,037,330 B1 | 5/2006 | Rivelli, Jr. et al. |
| 7,041,129 B2 | 5/2006 | Rourke et al. |
| 7,066,951 B2 | 6/2006 | Chobotov |
| 7,069,835 B2 | 7/2006 | Nishri et al. |
| 7,074,236 B2 | 7/2006 | Rabkin et al. |
| 7,093,527 B2 | 8/2006 | Rapaport et al. |
| 7,101,392 B2 | 9/2006 | Heath |
| 7,107,105 B2 | 9/2006 | Bjorklund et al. |
| 7,118,539 B2 | 10/2006 | Vrba et al. |
| 7,118,594 B2 | 10/2006 | Quiachon et al. |
| 7,122,050 B2 | 10/2006 | Randall et al. |
| 7,137,990 B2 | 11/2006 | Hebert et al. |
| 7,166,125 B1 | 1/2007 | Baker et al. |
| 7,169,170 B2 | 1/2007 | Widenhouse |
| 7,169,172 B2 | 1/2007 | Levine et al. |
| 7,172,617 B2 | 2/2007 | Colgan et al. |
| 7,192,434 B2 | 3/2007 | Anderson et al. |
| 7,195,639 B2 | 3/2007 | Quiachon et al. |
| 7,195,648 B2 | 3/2007 | Jones et al. |
| 7,201,768 B2 | 4/2007 | Diaz et al. |
| 7,201,769 B2 | 4/2007 | Jones et al. |
| 7,211,109 B2 | 5/2007 | Thompson |
| 7,213,495 B2 | 5/2007 | McCullagh et al. |
| 7,220,271 B2 | 5/2007 | Clubb et al. |
| 7,235,096 B1 | 6/2007 | Van Tassel et al. |
| 7,264,632 B2 | 9/2007 | Wright et al. |
| 7,275,471 B2 | 10/2007 | Nishri et al. |
| 7,279,005 B2 | 10/2007 | Stinson |
| 7,279,208 B1 | 10/2007 | Goffena et al. |
| 7,294,137 B2 | 11/2007 | Rivelli, Jr. et al. |
| 7,294,146 B2 | 11/2007 | Chew et al. |
| 7,300,456 B2 | 11/2007 | Andreas et al. |
| 7,300,460 B2 | 11/2007 | Levine et al. |
| 7,306,624 B2 | 12/2007 | Yodfat et al. |
| 7,309,351 B2 | 12/2007 | Escamilla et al. |
| 7,311,031 B2 | 12/2007 | McCullagh et al. |
| 7,320,702 B2 | 1/2008 | Hammersmark et al. |
| 7,323,001 B2 | 1/2008 | Clubb et al. |
| 7,331,973 B2 | 2/2008 | Gesswein et al. |
| 7,331,976 B2 | 2/2008 | McGuckin, Jr. et al. |
| 7,331,985 B2 | 2/2008 | Thompson et al. |
| 7,338,518 B2 | 3/2008 | Chobotov |
| 7,438,712 B2 | 10/2008 | Chouinard |
| 7,462,192 B2 | 12/2008 | Norton et al. |
| 7,468,070 B2 | 12/2008 | Henry et al. |
| 7,470,282 B2 | 12/2008 | Shelso |
| 7,473,271 B2 | 1/2009 | Gunderson |
| 7,491,224 B2 | 2/2009 | Cox et al. |
| 7,520,893 B2 | 4/2009 | Rivelli, Jr. |
| RE40,816 E | 6/2009 | Taylor et al. |
| 7,572,288 B2 | 8/2009 | Cox |
| 7,572,290 B2 | 8/2009 | Yodfat et al. |
| 7,588,597 B2 | 9/2009 | Frid |
| 7,695,507 B2 | 4/2010 | Rivelli, Jr. et al. |
| 7,763,011 B2 | 7/2010 | Ortiz et al. |
| 7,771,463 B2 | 8/2010 | Ton et al. |
| 7,854,760 B2 | 12/2010 | Molaei et al. |
| 7,901,447 B2 | 3/2011 | Molaei et al. |
| 7,942,925 B2 | 5/2011 | Yodfat et al. |
| 8,007,529 B2 | 8/2011 | Yan |
| 8,092,486 B2 | 1/2012 | Berrada et al. |
| 8,092,508 B2 | 1/2012 | Leynov et al. |
| 8,192,484 B2 | 6/2012 | Frid |
| 8,382,825 B2 | 2/2013 | Garcia et al. |
| 8,394,119 B2 | 3/2013 | Zaver et al. |
| 8,398,701 B2 | 3/2013 | Berez et al. |
| 8,617,234 B2 | 12/2013 | Garcia et al. |
| 8,623,067 B2 | 1/2014 | Berez et al. |
| 8,628,564 B2 | 1/2014 | Berez et al. |
| 8,764,817 B2 | 7/2014 | Sheldon |
| 8,801,772 B2 | 8/2014 | Shobayashi et al. |
| 8,979,918 B2 | 3/2015 | Murayama |
| 9,050,205 B2 | 6/2015 | Berez et al. |
| 9,114,001 B2 | 8/2015 | Kusleika et al. |
| 9,125,659 B2 | 9/2015 | Berez et al. |
| 9,157,174 B2 | 10/2015 | Kusleika |
| 2001/0027338 A1 | 10/2001 | Greenberg |
| 2001/0044651 A1 | 11/2001 | Steinke et al. |
| 2001/0049547 A1 | 12/2001 | Moore |
| 2001/0056299 A1 | 12/2001 | Thompson |
| 2002/0004667 A1 | 1/2002 | Adams et al. |
| 2002/0007194 A1 | 1/2002 | Plowiecki |
| 2002/0029061 A1 | 3/2002 | Amplatz et al. |
| 2002/0035396 A1 | 3/2002 | Heath |
| 2002/0062091 A1 | 5/2002 | Jacobsen et al. |
| 2002/0078808 A1 | 6/2002 | Jacobsen et al. |
| 2002/0082558 A1 | 6/2002 | Samson et al. |
| 2002/0087119 A1 | 7/2002 | Parodi |
| 2002/0111633 A1 | 8/2002 | Stoltze et al. |
| 2002/0111648 A1 | 8/2002 | Kusleika et al. |
| 2002/0120323 A1 | 8/2002 | Thompson et al. |
| 2002/0138133 A1 | 9/2002 | Lenz et al. |
| 2002/0143361 A1 | 10/2002 | Douk et al. |
| 2002/0143384 A1 | 10/2002 | Ozasa |
| 2002/0169473 A1 | 11/2002 | Sepetka et al. |
| 2002/0169474 A1 | 11/2002 | Kusleika et al. |
| 2002/0173839 A1 | 11/2002 | Leopold et al. |
| 2002/0188314 A1 | 12/2002 | Anderson et al. |
| 2002/0193864 A1 | 12/2002 | Khosravi et al. |
| 2003/0009215 A1 | 1/2003 | Mayer |
| 2003/0023299 A1 | 1/2003 | Amplatz et al. |
| 2003/0069522 A1 | 4/2003 | Jacobsen et al. |
| 2003/0100945 A1 | 5/2003 | Yodfat et al. |
| 2003/0130684 A1 | 7/2003 | Brady et al. |
| 2003/0135258 A1 | 7/2003 | Andreas et al. |
| 2003/0163155 A1 | 8/2003 | Haverkost et al. |
| 2003/0163156 A1 | 8/2003 | Hebert et al. |
| 2003/0176884 A1 | 9/2003 | Berrada et al. |
| 2003/0187495 A1 | 10/2003 | Cully et al. |
| 2003/0212429 A1 | 11/2003 | Keegan et al. |
| 2003/0212430 A1 | 11/2003 | Bose et al. |
| 2004/0024416 A1 | 2/2004 | Yodfat et al. |
| 2004/0030265 A1 | 2/2004 | Murayama et al. |
| 2004/0044395 A1 | 3/2004 | Nelson |
| 2004/0073300 A1 | 4/2004 | Chouinard et al. |
| 2004/0088037 A1 | 5/2004 | Nachreiner et al. |
| 2004/0093010 A1 | 5/2004 | Gesswein et al. |
| 2004/0098099 A1 | 5/2004 | McCullagh et al. |
| 2004/0133223 A1 | 7/2004 | Weber |
| 2004/0153117 A1 | 8/2004 | Clubb et al. |
| 2004/0162606 A1 | 8/2004 | Thompson |
| 2004/0172055 A1 | 9/2004 | Huter et al. |
| 2004/0186368 A1 | 9/2004 | Ramzipoor et al. |
| 2004/0193178 A1 | 9/2004 | Nikolchev |
| 2004/0193179 A1 | 9/2004 | Nikolchev |
| 2004/0193208 A1 | 9/2004 | Talpade et al. |
| 2004/0199243 A1 | 10/2004 | Yodfat |
| 2004/0210235 A1 | 10/2004 | Deshmukh et al. |

(56) References Cited

U.S. PATENT DOCUMENTS

| | | |
|---|---|---|
| 2004/0215332 A1 | 10/2004 | Frid |
| 2004/0220585 A1 | 11/2004 | Nikolchev |
| 2004/0220608 A1 | 11/2004 | D'Aquanni et al. |
| 2004/0220663 A1 | 11/2004 | Rivelli |
| 2004/0254628 A1 | 12/2004 | Nazzaro et al. |
| 2004/0260331 A1 | 12/2004 | D'Aquanni et al. |
| 2005/0004595 A1 | 1/2005 | Boyle et al. |
| 2005/0021075 A1 | 1/2005 | Bonnette et al. |
| 2005/0033407 A1 | 2/2005 | Weber et al. |
| 2005/0038447 A1 | 2/2005 | Huffmaster |
| 2005/0051243 A1 | 3/2005 | Forbes Jones et al. |
| 2005/0055047 A1 | 3/2005 | Greenhalgh |
| 2005/0059889 A1 | 3/2005 | Mayer |
| 2005/0060017 A1 | 3/2005 | Fischell et al. |
| 2005/0090888 A1 | 4/2005 | Hines et al. |
| 2005/0101989 A1 | 5/2005 | Cully et al. |
| 2005/0137680 A1 | 6/2005 | Ortiz et al. |
| 2005/0149111 A1 | 7/2005 | Kanazawa et al. |
| 2005/0165441 A1 | 7/2005 | McGuckin et al. |
| 2005/0177186 A1 | 8/2005 | Cully et al. |
| 2005/0192620 A1 | 9/2005 | Cully et al. |
| 2005/0197689 A1 | 9/2005 | Molaei |
| 2005/0209672 A1 | 9/2005 | George et al. |
| 2005/0209678 A1 | 9/2005 | Henkes et al. |
| 2005/0246010 A1 | 11/2005 | Alexander et al. |
| 2005/0267568 A1 | 12/2005 | Berez et al. |
| 2005/0283220 A1 | 12/2005 | Gobran et al. |
| 2005/0288764 A1 | 12/2005 | Snow et al. |
| 2005/0288766 A1 | 12/2005 | Plain et al. |
| 2006/0020324 A1 | 1/2006 | Schmid et al. |
| 2006/0036309 A1 | 2/2006 | Hebert et al. |
| 2006/0089703 A1 | 4/2006 | Escamilla et al. |
| 2006/0095213 A1 | 5/2006 | Escamilla et al. |
| 2006/0111771 A1 | 5/2006 | Ton et al. |
| 2006/0116713 A1 | 6/2006 | Sepetka et al. |
| 2006/0116750 A1 | 6/2006 | Hebert et al. |
| 2006/0184238 A1* | 8/2006 | Kaufmann ............... A61F 2/90 623/1.53 |
| 2006/0195118 A1 | 8/2006 | Richardson |
| 2006/0206148 A1 | 9/2006 | Khairkhahan et al. |
| 2006/0206200 A1 | 9/2006 | Garcia et al. |
| 2006/0206201 A1 | 9/2006 | Garcia et al. |
| 2006/0212127 A1 | 9/2006 | Karabey et al. |
| 2006/0271149 A1 | 11/2006 | Berez et al. |
| 2006/0271153 A1 | 11/2006 | Garcia et al. |
| 2006/0276910 A1 | 12/2006 | Weber |
| 2007/0021816 A1 | 1/2007 | Rudin |
| 2007/0043419 A1 | 2/2007 | Nikolchev et al. |
| 2007/0055365 A1 | 3/2007 | Greenberg et al. |
| 2007/0060994 A1 | 3/2007 | Gobran et al. |
| 2007/0073379 A1 | 3/2007 | Chang |
| 2007/0077347 A1 | 4/2007 | Richter |
| 2007/0100321 A1 | 5/2007 | Rudakov et al. |
| 2007/0100414 A1 | 5/2007 | Licata et al. |
| 2007/0100430 A1 | 5/2007 | Rudakov et al. |
| 2007/0112415 A1 | 5/2007 | Bartlett |
| 2007/0119295 A1 | 5/2007 | McCullagh et al. |
| 2007/0123969 A1 | 5/2007 | Gianotti |
| 2007/0162104 A1 | 7/2007 | Frid |
| 2007/0167980 A1 | 7/2007 | Figulla et al. |
| 2007/0198076 A1 | 8/2007 | Hebert et al. |
| 2007/0203559 A1 | 8/2007 | Freudenthal et al. |
| 2007/0203563 A1 | 8/2007 | Hebert et al. |
| 2007/0208367 A1 | 9/2007 | Fiorella et al. |
| 2007/0208373 A1 | 9/2007 | Zaver et al. |
| 2007/0208376 A1 | 9/2007 | Meng |
| 2007/0208415 A1 | 9/2007 | Grotheim et al. |
| 2007/0219619 A1 | 9/2007 | Dieck et al. |
| 2007/0225760 A1 | 9/2007 | Moszner et al. |
| 2007/0233175 A1 | 10/2007 | Zaver et al. |
| 2007/0239261 A1 | 10/2007 | Bose et al. |
| 2007/0255386 A1 | 11/2007 | Tenne |
| 2007/0255388 A1 | 11/2007 | Rudakov et al. |
| 2007/0280850 A1 | 12/2007 | Carlson |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0015673 A1 | 1/2008 | Chuter |
| 2008/0033341 A1 | 2/2008 | Grad |
| 2008/0033526 A1 | 2/2008 | Atladottir et al. |
| 2008/0039930 A1 | 2/2008 | Jones et al. |
| 2008/0039933 A1 | 2/2008 | Yodfat et al. |
| 2008/0071351 A1 | 3/2008 | Flanagan et al. |
| 2008/0082154 A1 | 4/2008 | Tseng et al. |
| 2008/0114391 A1 | 5/2008 | Dieck et al. |
| 2008/0119943 A1 | 5/2008 | Armstrong et al. |
| 2008/0125855 A1 | 5/2008 | Henkes et al. |
| 2008/0208320 A1 | 8/2008 | Tan-Malecki et al. |
| 2008/0221666 A1 | 9/2008 | Licata et al. |
| 2008/0221670 A1 | 9/2008 | Clerc et al. |
| 2008/0221671 A1 | 9/2008 | Chouinard et al. |
| 2008/0255654 A1 | 10/2008 | Hebert et al. |
| 2008/0255655 A1 | 10/2008 | Kusleika et al. |
| 2008/0262590 A1 | 10/2008 | Murray |
| 2008/0269774 A1 | 10/2008 | Garcia et al. |
| 2008/0275497 A1 | 11/2008 | Palmer et al. |
| 2008/0275498 A1 | 11/2008 | Palmer et al. |
| 2008/0294104 A1 | 11/2008 | Mawad |
| 2008/0300667 A1 | 12/2008 | Hebert et al. |
| 2008/0300668 A1 | 12/2008 | Bonsignore |
| 2008/0300673 A1 | 12/2008 | Clerc et al. |
| 2009/0024202 A1 | 1/2009 | Dave et al. |
| 2009/0024205 A1 | 1/2009 | Hebert et al. |
| 2009/0030496 A1 | 1/2009 | Kaufmann et al. |
| 2009/0030497 A1 | 1/2009 | Metcalf et al. |
| 2009/0054981 A1 | 2/2009 | Frid et al. |
| 2009/0099643 A1 | 4/2009 | Hyodoh et al. |
| 2009/0105802 A1 | 4/2009 | Henry et al. |
| 2009/0105803 A1 | 4/2009 | Shelso |
| 2009/0125093 A1 | 5/2009 | Hansen |
| 2009/0192536 A1 | 7/2009 | Berez et al. |
| 2009/0192587 A1 | 7/2009 | Frid |
| 2009/0198318 A1 | 8/2009 | Berez et al. |
| 2009/0216307 A1 | 8/2009 | Kaufmann et al. |
| 2009/0222035 A1 | 9/2009 | Schneiderman |
| 2009/0270974 A1 | 10/2009 | Berez et al. |
| 2009/0287241 A1 | 11/2009 | Berez et al. |
| 2009/0287288 A1 | 11/2009 | Berez et al. |
| 2009/0288000 A1 | 11/2009 | McPherson |
| 2009/0292348 A1 | 11/2009 | Berez et al. |
| 2009/0318947 A1 | 12/2009 | Garcia et al. |
| 2009/0319017 A1 | 12/2009 | Berez et al. |
| 2010/0010624 A1 | 1/2010 | Berez et al. |
| 2010/0042200 A1* | 2/2010 | Richter ............... A61F 2/86 623/1.11 |
| 2010/0061604 A1 | 3/2010 | Nahm et al. |
| 2010/0063531 A1 | 3/2010 | Rudakov et al. |
| 2010/0070024 A1 | 3/2010 | Venturelli et al. |
| 2010/0076317 A1 | 3/2010 | Babic et al. |
| 2010/0152834 A1 | 6/2010 | Hannes et al. |
| 2010/0161025 A1 | 6/2010 | Kuppurathanam et al. |
| 2010/0174269 A1 | 7/2010 | Tompkins et al. |
| 2010/0174309 A1 | 7/2010 | Fulkerson et al. |
| 2010/0179583 A1 | 7/2010 | Carpenter et al. |
| 2010/0179647 A1 | 7/2010 | Carpenter et al. |
| 2010/0198334 A1 | 8/2010 | Yodfat et al. |
| 2010/0204779 A1 | 8/2010 | Schuessler et al. |
| 2010/0211154 A1 | 8/2010 | Murayama |
| 2010/0222864 A1 | 9/2010 | Rivelli, Jr. et al. |
| 2010/0241214 A1 | 9/2010 | Holzer et al. |
| 2010/0256732 A1 | 10/2010 | Shin et al. |
| 2010/0256733 A1 | 10/2010 | Schuessler |
| 2010/0280587 A1 | 11/2010 | Ortiz et al. |
| 2010/0318174 A1 | 12/2010 | Shaolian et al. |
| 2010/0318178 A1 | 12/2010 | Rapaport et al. |
| 2011/0016427 A1 | 1/2011 | Douen |
| 2011/0040372 A1 | 2/2011 | Hansen et al. |
| 2011/0046718 A1 | 2/2011 | Cattaneo et al. |
| 2011/0046720 A1* | 2/2011 | Shalev et al. ............... 623/1.18 |
| 2011/0054589 A1 | 3/2011 | Bashiri et al. |
| 2011/0166592 A1 | 7/2011 | Garcia et al. |
| 2011/0166637 A1 | 7/2011 | Irwin et al. |
| 2011/0166639 A1 | 7/2011 | Pulnev et al. |
| 2011/0179389 A1 | 7/2011 | Douen |

(56) References Cited

U.S. PATENT DOCUMENTS

| | | |
|---|---|---|
| 2011/0184451 A1 | 7/2011 | Sahl |
| 2011/0190862 A1 | 8/2011 | Bashiri et al. |
| 2011/0245862 A1 | 10/2011 | Dieck et al. |
| 2011/0270178 A1 | 11/2011 | Fiorella et al. |
| 2012/0035643 A1 | 2/2012 | Khairkhahan et al. |
| 2012/0041459 A1 | 2/2012 | Fiorella et al. |
| 2012/0158124 A1 | 6/2012 | Zaver et al. |
| 2012/0253454 A1* | 10/2012 | Costello ............ 623/1.34 |
| 2012/0290067 A1 | 11/2012 | Cam et al. |
| 2012/0316638 A1 | 12/2012 | Grad et al. |
| 2012/0323309 A1 | 12/2012 | Cattaneo |
| 2013/0116773 A1 | 5/2013 | Roeder et al. |
| 2013/0123901 A1 | 5/2013 | Connor et al. |
| 2013/0138202 A1 | 5/2013 | Paul et al. |
| 2013/0172975 A1 | 7/2013 | Berez et al. |
| 2013/0190856 A1 | 7/2013 | von Oepen et al. |
| 2013/0204347 A1 | 8/2013 | Armstrong et al. |
| 2013/0211489 A1 | 8/2013 | Makower et al. |
| 2013/0211497 A1 | 8/2013 | Charlebois et al. |
| 2013/0274849 A1 | 10/2013 | Zaver et al. |
| 2014/0018843 A1 | 1/2014 | Berez et al. |
| 2014/0074149 A1 | 3/2014 | Garcia et al. |
| 2014/0121744 A1 | 5/2014 | Kusleika |
| 2014/0121746 A1 | 5/2014 | Kusleika et al. |
| 2014/0316454 A1 | 10/2014 | Zaver et al. |
| 2014/0336741 A1 | 11/2014 | Connor et al. |
| 2015/0359646 A1 | 12/2015 | Kusleika et al. |

FOREIGN PATENT DOCUMENTS

| | | |
|---|---|---|
| EP | 1683541 A2 | 7/2006 |
| EP | 1942972 | 7/2008 |
| EP | 1872742 B1 | 5/2009 |
| EP | 2 078 512 A1 | 7/2009 |
| FR | 2556210 | 6/1985 |
| JP | 10-328216 A | 12/1998 |
| JP | 11-506686 | 6/1999 |
| JP | 11-299901 A | 11/1999 |
| JP | 2001-509412 A | 7/2001 |
| JP | 2002-253682 | 9/2002 |
| JP | 2003520103 A | 7/2003 |
| JP | 2004-049585 A | 2/2004 |
| JP | 2005-074230 A | 3/2005 |
| JP | 2006-506201 A | 2/2006 |
| JP | 2008-541832 A | 11/2008 |
| WO | WO-88/00813 | 2/1988 |
| WO | WO-95/009586 | 4/1995 |
| WO | WO-95/032757 | 12/1995 |
| WO | WO-98/004211 | 2/1998 |
| WO | 98/47447 A1 | 10/1998 |
| WO | WO-99/002092 | 1/1999 |
| WO | 99/05977 A1 | 2/1999 |
| WO | WO-99/049812 A3 | 12/1999 |
| WO | WO-01/005331 | 1/2001 |
| WO | WO-01/052771 | 7/2001 |
| WO | WO-02/005729 | 1/2002 |
| WO | WO-02/047579 | 6/2002 |
| WO | WO-02/054988 A3 | 1/2003 |
| WO | WO-03/007840 A2 | 1/2003 |
| WO | WO-03/043527 A2 | 5/2003 |
| WO | WO-03/049600 A2 | 6/2003 |
| WO | 03/057079 A1 | 7/2003 |
| WO | WO-03/073963 A2 | 9/2003 |
| WO | WO-2004/087006 A3 | 11/2004 |
| WO | WO 2005/021061 | 3/2005 |
| WO | WO-2005/023149 A3 | 12/2005 |
| WO | 2006/034140 A2 | 3/2006 |
| WO | WO-2006/073745 A2 | 7/2006 |
| WO | WO-2006/127005 | 11/2006 |
| WO | 2007/122396 A1 | 11/2007 |
| WO | 2008/005898 A2 | 1/2008 |
| WO | WO-2007/139689 A3 | 9/2008 |
| WO | WO-2007/139699 A3 | 9/2008 |
| WO | WO 2008/156683 | 12/2008 |
| WO | WO-2005/115118 A3 | 7/2009 |
| WO | WO-2009/105710 | 8/2009 |
| WO | 2010/127838 A2 | 11/2010 |
| WO | 2011/023105 A1 | 3/2011 |
| WO | 2011/134663 | 11/2011 |

OTHER PUBLICATIONS

Brilstra, et al., Treatment of Intracranial Aneurysms by Embolization with Coils: A Systematic Review, Stroke, Journal of the American Heart Association, 1999, vol. 30, pp. 470-476.

Ferguson, Gary, Physical Factors in the Initiation, Growth and Rupture of Human Intracranial Saccular Ameurysms, J. Neurosurg, Dec. 1972, vol. 37, pp. 666-667.

Geremia, et al., Embolization of Experimentally Created Aneurysms with Intravascular Stent Devices, ANJR American Journal of Neuroradiology, Aug. 1994, vol. 15, pp. 1223-1231.

Geremia, et al., Occlusion of Experimentally Created Fusiform Aneurysms with Porous Metallic Stents, ANJR Am J Neuroradiol, Apr. 2000, Issue 21, pp. 739-745.

Lanzino, et al., Efficacy and Current Limitations of Intravascular Stents for Intracranial Internal Carotid, Vertebral, and Basilar Artery Aneurysms, Journal of Neurosurgery, Oct. 1999, vol. 91, Issue 4, pp. 538-546.

Lieber, et al., Alteration of Hemodynamics in Aneurysm Models by Stenting: Influence of Stent Porosity, Ann of Biomedical Eng., 1997, vol. 25, pp. 460-469, Buffalo, NY.

Lieber, et al., The Physics of Endoluminal Stenting in the Treatment of Cerebrovascular Aneurysms, Neurological Research, 2002, Vcol 24, Issue Supplement 1, pp. S32-S42.

Moss, et al., Vascular Occlusion with a Balloon-Expadable Stent Occluder, Radiology, May 1994, vol. 191, Issue 2, pp. 483-486.

Pereira, Edgard, History of Endovascular Aneurysm Occlusion, Management of Cerebral Aneurysms, 2004, pp. 11-26.

Qureshi, Adnan, Endovascular Treatment of Cerebrovascular Diseases and Intracranial Neoplasms, The Lancelet, Mar. 2004, vol. 363, pp. 804-813.

Steiger, Pathophysiology of Development and Rupture of Cerebral Aneurysms, Acta Nurochirurgica, Mar. 1990, Vol Supplementum 48, Pages in 62 pages.

Tenaglia, et al., Ultrasound Guide Wire-Directed Stent Deployment, Duke University Medical Center, Department of Medicine, 1993 USA.

Yu, et al., A Steady Flow Analysis on the Stented and Non-Stented Sidewall Aneurysm Models, Medical Engineering and Physics, Apr. 1999, Issue 21, pp. 133-141.

U.S. Appl. No. 13/644,854, filed Oct. 31, 2012.
U.S. Appl. No. 13/669,944, filed Nov. 6, 2012.
U.S. Appl. No. 13/826,971, filed Mar. 14, 2013.
U.S. Appl. No. 13/775,592, filed Feb. 25, 2013.
U.S. Appl. No. 13/845,162, filed Mar. 18, 2013.
U.S. Appl. No. 13/827,030, filed Mar. 14, 2013.
U.S. Appl. No. 13/826,147, filed Mar. 14, 2013.

* cited by examiner

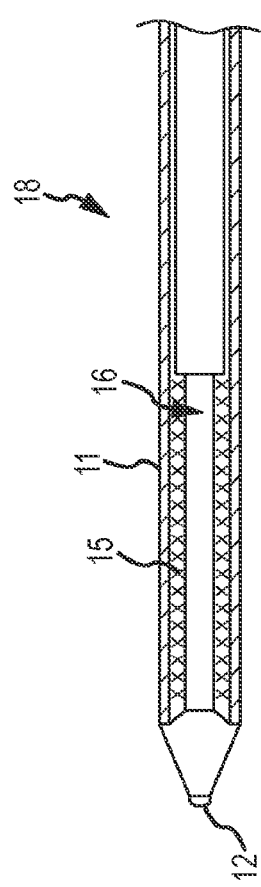
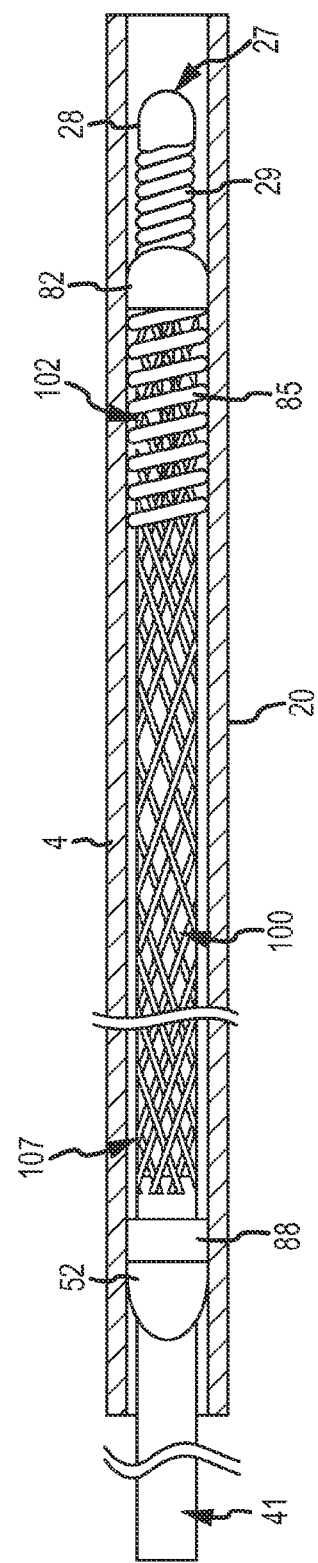
FIG.4a
FIG.4b

SHAPED OCCLUDING DEVICES AND METHODS OF USING THE SAME

BACKGROUND

Lumens in the body can change in size, shape, and/or patency, and such changes can present complications or affect associated body functions. For example, the walls of the vasculature, particularly arterial walls, may develop pathological dilatation called an aneurysm. Aneurysms are observed as a ballooning of the wall of an artery. This is a result of the vessel wall being weakened by disease, injury, or a congenital abnormality. Aneurysms have thin, weak walls and have a tendency to rupture and are often caused or made worse by high blood pressure. Aneurysms can be found in different parts of the body; the most common being abdominal aortic aneurysms (AAA) and the brain or cerebral aneurysms. The mere presence of an aneurysm is not always life-threatening, but they can have serious heath consequences such as a stroke if one should rupture in the brain. Additionally, a ruptured aneurysm can also result in death.

Vascular devices or "occluding devices" such as stents are often used to treat patients with aneurysms. Stent and/or other occluding devices can be implanted within the vasculature of a patient by a delivery system such as a catheter. Precise and accurate positioning of these vascular devices at a target site is often required before a stent can be safely and effectively detached from the stent delivery system to a target site within a patient's vasculature. Positioning can be a delicate process that may require positioning and re-positioning of the stent delivery device prior to the detachment of the stent.

SUMMARY

In an aneurysm there may occur naturally high pressure and flow against the distal lateral wall of the aneurysm sac. This high pressure and flow can contribute to aneurysm growth and may eventually lead to aneurysm failure, even in the presence of a stent or occluding device. The self-expanding stents disclosed herein modulate the flow dynamics to reduce the flow and pressure exerted at the distal lateral wall of the aneurysm to reduce risk of sac rupture. In some embodiments, this is achieved via a narrowed or constricted portion of the self-expanding stent. The narrowed portion may be disposed within the vessel at a location between the distal and proximal walls of the aneurysm neck or aneurysm ostium and, in particular, the narrowed portion may abut the distal lateral wall. Thus, embodiments disclosed herein advantageously provide self-expanding stents that are shaped to be capable of reducing the flow and pressure exerted against the distal lateral wall of the aneurysm by altering the flow dynamics within the vessel and aneurysm.

In some embodiments described herein, a self-expanding stent comprises a proximal portion having a first cross-sectional area in an expanded state, a distal portion having a second cross-sectional area in an expanded state, and a narrowed portion between the proximal portion and the distal portion, the narrowed portion comprising a cross-sectional area when in an expanded state that is less than the first cross-sectional area and the second cross-sectional area, wherein the narrowed portion is configured to increases flow velocity in the narrowed portion while reducing reduce pressure against a distal wall of the aneurysm by being axially disposed substantially between a proximal edge and a distal edge of an aneurysm neck or ostium, the flow traversing through the lumen of the self-expanding stent.

In some embodiments described herein, a self-expanding stent comprises a proximal portion having a first cross-sectional area in an expanded state, a distal portion having a second cross-sectional area in an expanded state, a narrowed portion between the proximal portion and the distal portion, the narrowed portion comprising a cross-sectional area when in an expanded state that is less than the first cross-sectional area and the second cross-sectional area, wherein the narrowed portion is configured to reduce the flow toward and pressure against a distal wall of the aneurysm by being axially disposed substantially between a proximal edge and a distal edge of an aneurysm neck or ostium, the flow traversing through the lumen of the self-expanding stent.

In some embodiments, the first cross-sectional area is larger than the second cross-sectional area. In some embodiments, the first cross-sectional area is selected to allow the stent to protrude into the aneurysm sac in the expanded state. In some embodiments, the first cross-sectional area and the second cross-sectional area are approximately equal. In some embodiments, the narrowed portion is circumferentially uniform. In some embodiments, the proximal and distal portions each have respective first and second central longitudinal axes that are substantially axially aligned, and the narrowed portion has a central longitudinal axis that is axially offset from the first and second longitudinal axes.

In some embodiments, the narrowed portion comprises a braid density that is greater than a braid density of the proximal portion and the distal portion. In some embodiments, the narrowed portion further comprises a coating. In some embodiments, the self-expanding stent further comprises a radio opaque marker disposed at a proximal end of the distal portion where the self-expanding stent transitions to the narrowed portion. In some embodiments, the first cross-sectional area and the second cross-sectional area are substantially circular, and the first cross-sectional area has a first diameter and the second cross-sectional area has a second diameter. In some embodiments, the narrowed portion has a greatest cross-sectional dimension less than the first diameter and the second diameter.

Some embodiments described herein relate to a system comprising a self-expanding stent comprising, the stent comprising a proximal portion having a first cross-sectional area in an expanded state, a distal portion having a second cross-sectional area in an expanded state, a narrowed portion between the proximal portion and the distal portion, the narrowed portion comprising a cross-sectional area when in an expanded state that is less than the first cross-sectional area and the second cross-sectional area, wherein the narrowed portion is configured to reduce the flow toward and pressure against a distal wall of an aneurysm by being axially disposed substantially between a proximal edge and a distal edge of an aneurysm neck or ostium, the flow traversing through the lumen of the self-expanding stent and the system further comprising a stent delivery device configured to position and release the self-expanding stent.

In some embodiments, the first cross-sectional area is larger than the second cross-sectional area. In some embodiments, the first cross-sectional area is selected to allow the stent to protrude into the aneurysm sac in the expanded state. In some embodiments, the first cross-sectional area and the second cross-sectional area are approximately equal. In some embodiments, the narrowed portion is circumferentially uniform. In some embodiments, the proximal portion has a first central longitudinal axis that is substantially aligned with a distal portion second central longitudinal axis, and the narrowed portion has a third central longitudinal axis that is axially offset from the first and second longitudinal axes.

In some embodiments, the narrowed portion comprises a braid density that is greater than a braid density of the proximal portion and the distal portion. In some embodiments, the narrowed portion further comprises a coating. In some embodiments, the self-expanding stent further comprises a radio opaque marker disposed at a proximal end of the distal portion where the self-expanding stent transitions to the narrowed portion. In some embodiments, the first cross-sectional area and the second cross-sectional area are substantially circular, and wherein the first cross-sectional area has a first diameter and the second cross-sectional area has a second diameter. In some embodiments, the narrowed portion has a greatest cross-sectional dimension less than the first diameter and the second diameter.

Some methods of treating an aneurysm described herein comprise positioning a self-expanding stent at an aneurysm, the self-expanding stent comprising a proximal portion having a first cross-sectional area in an expanded state, a distal portion having a second cross-sectional area in an expanded state, a narrowed portion between the proximal portion and the distal portion, the narrowed portion comprising a cross-sectional area when in an expanded state that is less than the first cross-sectional area and the second cross-sectional area, wherein the narrowed portion is configured to reduce the flow toward and pressure against a distal wall of the aneurysm by being axially disposed substantially between a proximal edge and a distal edge of an aneurysm neck or ostium, the flow traversing through the lumen of the self-expanding stent, and the method comprising expanding the self-expanding stent.

In some embodiments, the first cross-sectional area is larger than the second cross-sectional area. In some embodiments, the first cross-sectional area is selected to allow the stent to protrude into the aneurysm sac in the expanded state. In some embodiments, the first cross-sectional area and the second cross-sectional area are approximately equal. In some embodiments, the narrowed portion is circumferentially uniform, and wherein the positioning step comprises axially aligning the narrow portion along a central longitudinal axis of at least one of the proximal or distal portions. In some embodiments, the proximal, distal, and narrow portions each have respective first, second, and third central longitudinal axes, and wherein the positioning step comprises positioning the stent such that the first and second longitudinal axes are substantially axially aligned and the third longitudinal axis is axially offset from the first and second longitudinal axes.

In some embodiments, the narrowed portion comprises a braid density that is greater than the braid density of the proximal portion and the distal portion. In some embodiments, the narrowed portion further comprises a coating. In some embodiments, the positioning step comprises aligning a radio opaque marker, disposed at a proximal end of the distal portion on the self-expanding stent, with the distal wall of the aneurysm. In some embodiments, the first cross-sectional area and the second cross-sectional area are substantially circular, and wherein the first cross-sectional area has a first diameter and the second cross-sectional area has a second diameter. In some embodiments, the narrowed portion has a greatest cross-sectional dimension less than the first diameter and the second diameter.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

FIG. 4a shows a system for delivery of self-expanding stents, in accordance with some embodiments.

FIG. 4b shows another system for delivery of self-expanding stents, in accordance with some embodiments.

DETAILED DESCRIPTION

In the following detailed description, numerous specific details are set forth to provide a full understanding of the subject technology. It will be apparent, however, to one ordinarily skilled in the art that the subject technology may be practiced without some of these specific details. In other instances, well-known structures and techniques have not been shown in detail so as not to obscure the subject technology.

Figure 1:
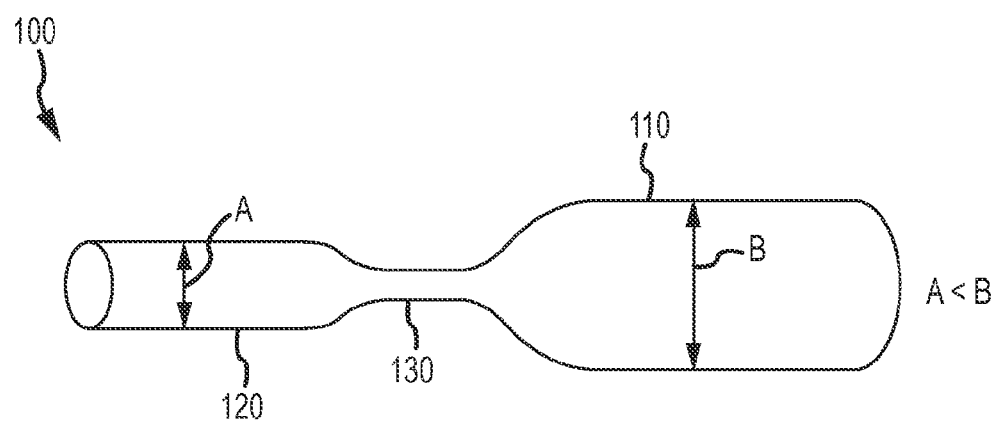
FIG. 1 shows a self-expanding stent, in accordance with some embodiments.
Figure 2:
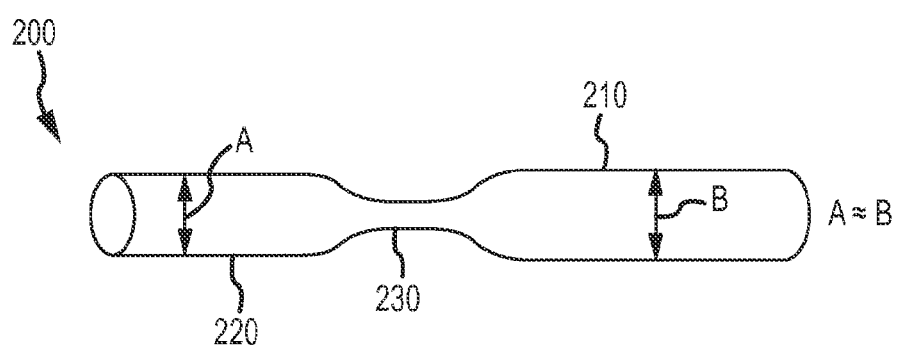
FIG. 2 shows another self-expanding stent, in accordance with some embodiments.
Figure 3:
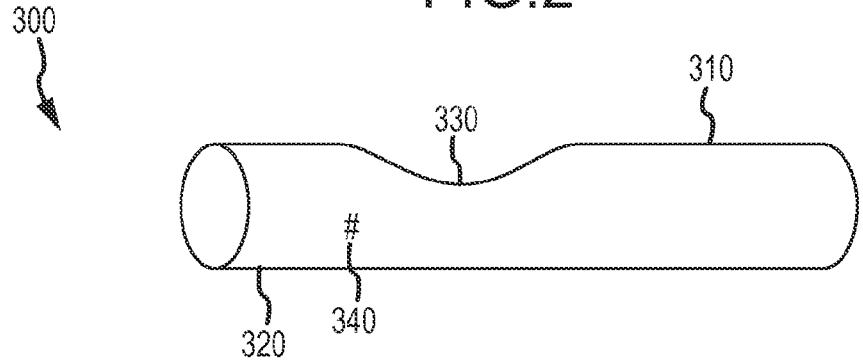
FIG. 3 shows yet another self-expanding stent, in accordance with some embodiments.

In an aneurysm there may occur naturally high pressure and flow against the distal lateral wall of the aneurysm sac. This high pressure and flow can contribute to aneurysm growth and may eventually lead to aneurysm failure, even in the presence of a stent or occluding device. Of the numerous advantages of embodiments of the subject technology, the self-expanding stents disclosed herein, exemplified in FIGS. 1-3, are shaped in a manner that may reduce the flow and pressure exerted at the distal lateral wall of the aneurysm to reduce risk of sac rupture. In some embodiments, this is achieved via a narrowed or constricted portion (e.g. 130, 230, 330, respectively in FIGS. 1-3) of the self-expanding stents 100, 200, and 300 in FIGS. 1-3. The narrowed portion may be disposed within the vessel at a location between the distal and proximal walls of the aneurysm neck or aneurysm ostium and, in particular, the narrowed portion may abut the distal lateral wall. Thus, embodiments disclosed herein advantageously provide self-expanding stents that are shaped to be capable of reducing the flow and pressure exerted against the distal lateral wall of the aneurysm by altering the flow dynamics within the vessel and aneurysm. In some embodiments, the narrowed portion may extend beyond the distal lateral wall of the aneurysm. In doing so, the increased flow velocity through the narrowed portion bypasses the aneurysm, effectively alleviating the stresses normally experienced on the distal later wall.

In some embodiments, a system for treating an aneurysm includes self-expanding stents, as exemplified in FIGS. 1-3, the self-expanding stents comprising a proximal portion having a first cross-sectional area in an expanded state, a distal portion having a second cross-sectional area in an expanded state, a narrowed portion between the proximal portion and the distal portion, the narrowed portion comprising a cross-sectional area when in an expanded state that is less than the first cross-sectional area and the second cross-sectional area, wherein the narrowed portion is configured to reduce the flow toward and pressure against a distal wall of an aneurysm neck or ostium by being axially disposed substantially between a proximal edge and a distal edge of an aneurysm neck or ostium, and the system further comprising a stent delivery device configured to position and release the self-expanding stent.

In an exemplary delivery system 18 shown in FIG. 4*a*, the self-expanding stent 15, in collapsed form, may be confined within the annular space between two telescoping tubes 11, 16. Guidewire lumen 12 is provided through the inner tube 16, the inner tube having a reduced diameter distal region to provide sufficient annular space in which self-expanding stent 15 is housed. Radiopaque markers may be provided at various locations along the length of the delivery system. In one example, the enlarged distal tip of inner tube 16 is radiopaque. In another example radiopaque markers are provided on the reduced diameter distal region of inner tube 16 beneath each end of the stent. In some embodiments, the self-expanding stent may also be provided with one or more radiopaque markers. In some embodiments, only the self-expanding stent may be provided with one or more radiopaque markers, while the delivery device is devoid of radiopaque markers.

Referring to FIG. 4*b*, illustrated is an exemplary stent delivery system 20 including a stent 100 carried by a core wire 41 as arranged within an introducer sheath or catheter 4. The stent 100 and the core wire 41 may be cooperatively movable within the catheter 4 in order to deliver the stent 100 to a predetermined treatment site, such as an aneurysm, within the vasculature of a patient. Accordingly, the catheter 4 may be configured to be introduced and advanced through the vasculature of the patient. The catheter 4 may be made from various thermoplastics, e.g., PTFE, FEP, HDPE, PEEK, etc., which may optionally be lined on the inner surface of the catheter 4 or an adjacent surface with a hydrophilic material such as PVP or some other plastic coating. Additionally, either surface may be coated with various combinations of different materials, depending upon the desired results.

The stent 100 may be characterized as a vascular occluding device and/or an embolization device, as generally known in the art. These terms are broad terms and are intended to have their ordinary meaning and include, unless expressly otherwise stated or incompatible with the description of, each of the stents and other vascular devices described herein. In some embodiments, the stent 100 may be a self-expanding stent made of two or more round or ovoid wire filaments. The filaments may be formed of known flexible materials including shape memory materials, such as nitinol, platinum, and stainless steel. In some embodiments, the stent 100 is fabricated from platinum/8% tungsten and 35N LT (cobalt nickel alloy, which is a low titanium version of MP35N alloy) alloy wires. In other embodiments, one or more of the filaments can be formed of a biocompatible metal material or a biocompatible polymer.

The wire filaments may be braided into a resulting lattice-like structure. In at least one embodiment, during braiding or winding of the stent 100, the filaments may be loosely braided using a 1-over-2-under-2 system. In other embodiments, however, other methods of braiding may be followed, without departing from the scope of the disclosure. The stent 100 may exhibit a porosity configured to reduce haemodynamic flow into, for example, an aneurysm, but simultaneously allow perfusion to an adjacent branch vessel. As will be appreciated, the porosity of the stent 100 may be adjusted by "packing" the stent during deployment, as known in the art. The ends of the stent 100 may be cut to length and therefore remain free for radial expansion and contraction. The stent 100 may exhibit a high degree of flexibility due to the materials used, the density (i.e., the porosity) of the filaments, and the fact that the ends are not secured.

The flexibility of the core wire 41 allows the stent delivery system 20 to bend and conform to the curvature of the vasculature as needed for positional movement of the stent 100 within the vasculature. The core wire 41 may be made of a conventional guidewire material and have a solid cross-section. Alternatively, the core wire 41 can be formed from a hypotube. The material used for the core wire 41 can be any of the known guidewire materials including superelastic metals or shape memory alloys, e.g., nitinol. Alternatively, the core wire 41 can be formed of metals such as stainless steel.

In one or more embodiments, the stent delivery system 20 may exhibit the same degree of flexion along its entire length. In other embodiments, however, the stent delivery system 20 can have two or more longitudinal sections, each with differing degrees of flexion/stiffness. The different degrees of flexions for the stent delivery system 20 can be created using different materials and/or thicknesses within different longitudinal sections of the core wire 41. In some embodiments, the flexion of the core wire 41 can be controlled by spaced cuts (not shown) formed within the core wire 41. These cuts can be longitudinally and/or circumferentially spaced from each other.

A tip 28 and flexible tip coil 29 may be secured to the distal end 27 of the delivery core wire 41. The tip 28 can be characterized as a distal solder joint formed of a continuous end cap or cover as shown in the figures, which securely receives a distal end of the tip coil 29. Flexion control is provided to the distal end 27 of the delivery core wire 41 by the tip coil 29. However, in an embodiment, the tip 28 can be free of the coil 29. As illustrated, the tip 28 may have a non-percutaneous, atraumatic end face. The tip coil 29 may be configured to surround at least a portion of the core wire 41. The tip coil 29 is flexible so that it will conform to and follow the path of a vessel within the patient as the tip 28 is advanced along the vessel and the core wire 41 bends to follow the tortuous path of the vasculature.

At the proximal end 107 of the stent 100, a proximal solder joint 52 and proximal marker 88 prevent or limit lateral movement of the stent 100 along the length of the core wire 41 in the direction of the proximal end 107. As illustrated, the proximal end 107 of the stent 100 may be axially-offset from the proximal marker 88 by a short distance. In other embodiments, however, the stent 100 may shift axially during introduction into the vasculature of the patient and contact the proximal marker 88 which prevents or limits the stent 100 from moving along the length of the core wire 41 away from a distally-located protective coil 85 coupled to an adjacent or mid solder joint 82.

After navigating the length of the catheter 4 to the predetermined treatment site within the patient, the stent 100 may be deployed from the catheter 4 in a variety of ways. In one embodiment, the catheter 4 is retracted while maintaining the position of the core wire 41 to expose the distal end 27 of the delivery core wire 41 and the distal end 102 of the stent 100. Upon exiting the catheter 4, the portion of the stent 100 that is not situated between the protective coil 85 and the core wire 41 and that is not covered by the catheter 4 begins to expand radially. The catheter 4 may then be further retracted until enough of the stent 100 is exposed such that the expansion diameter of the stent 100 is sufficient to engage the walls of the vessel (not shown), such as a blood vessel. Upon engaging a portion of said vessel, the stent 100 may be at least partially anchored within the vessel.

The core wire 41 may then be rotated at its proximal end, which causes rotation at the distal end 27 relative to the stent 100. The rotation of the core wire 41 also causes twisting of the protective coil 85, which pushes the distal end 102 of the stent 100 out from beneath the protective coil 85 like a corkscrew. Once the distal end 102 of the stent 100 is released from the protective coil 85, it expands to engage the walls of the vessel. The catheter 4 may then be further retracted to expose and expand the remaining portions of the stent 100.

Those skilled in the art will readily recognize that variations of this deployment method are possible. For example, the catheter 4 may be further retracted before rotating the core wire 41, such as by expanding the proximal end 107 of the stent 100 before expanding the distal end 102. Other examples of deployment variations include causing or otherwise creating variable porosity of the stent 100.

Once the entire stent 100 is expanded, the core wire 41 may then be retracted back into the catheter 4 by pulling proximally on the core wire 41 and maintaining the catheter 4 in its position. The proximal taper of the solder joint 52 coupled to the proximal marker 88 helps guide retraction of the core wire 41 back into the catheter 4. The core wire 41 and the catheter 4 may then be both retracted from the vessel and vasculature of the patient.

Figure 5:
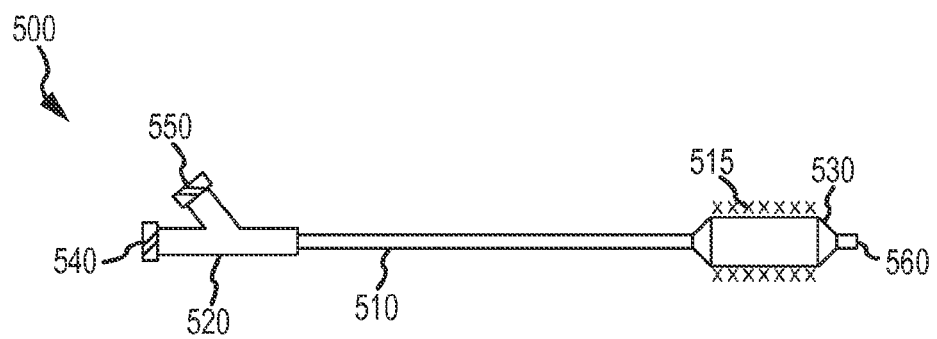
FIG. 5 shows an over the wire (OTW) balloon catheter delivery device, in accordance with some embodiments.
Figure 6:
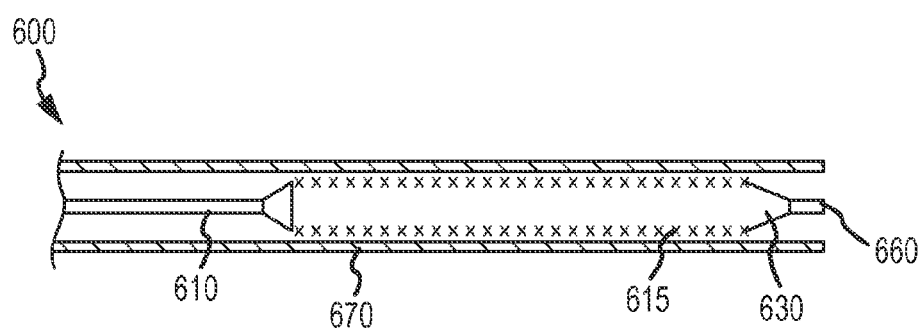
FIG. 6 shows another OTW balloon catheter delivery device, in accordance with some embodiments.

Referring now to FIGS. 5 and 6, in some embodiments, the self-expanding stent may be delivered and deployed using a balloon catheter. The balloon catheter can have an over the wire (OTW) configuration, a rapid exchange (multiple lumen) configuration, or a fixed wire configuration. Referring to FIG. 5, in some embodiments, an OTW balloon catheter 500 may comprise a shaft 510 having a guide wire lumen (internally) to which is affixed manifold 520 and balloon 530. Shaft 510 can be equipped with two lumens, one for the guide wire and one for inflating balloon 530. At the proximal end of each lumen a manifold hub 540 and 550 may be attached to shaft 510, as indicated in FIG. 5.

In some embodiments, the self-expanding stent may be mounted to a balloon either with or without adhesive. As indicated in FIG. 6, in such a delivery configuration, at least the distal portion of the stent delivery system 600 may be contained within a sheath 670, which retains the self-expanding stent 615 and balloon 630 in an axial elongated and diametrically reduced configuration. When deploying self-expanding stent 615, sheath 670 can be withdrawn proximally and balloon 630 and self-expanding stent 615 may be radially expanded and longitudinally shortened.

Figure 7:
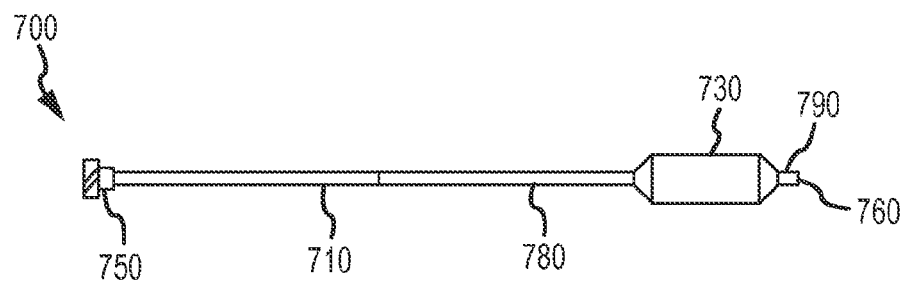
FIG. 7 shows a rapid exchange configuration balloon catheter delivery device, in accordance with some embodiments.

Referring now to FIG. 7, in some embodiments, a balloon catheter 700 can be used having a rapid exchange configuration comprising shaft 710 having a guidewire lumen (internal) to which is affixed a hub 750 and a balloon 730. Shaft 710 may have two lumens over the distal region only. The guidewire lumen runs from the distal end to a skive 780 at which the guidewire lumen terminates and communicates with the exterior of the catheter. The second lumen runs from hub 750 to balloon 730 interior and is used for inflating the balloon.

In some embodiments, the balloon catheter delivery device may have a fixed wire configuration comprising a shaft having an inflation lumen only, to which is affixed a hub and a balloon. In some embodiments, the balloon catheter may be a perfusing design whereby during balloon inflation, blood can bypass the balloon thereby perfusing tissues downstream of the obstruction caused by the balloon. Perfusing balloons can be useful for systems that rely on dissolution of an attachment between the balloon and the stent.

When employing delivery devices comprising balloon catheters, such balloons may have an inner member beneath the balloon that axially shrinks during balloon inflation by the same amount as the axial shrinkage of the balloon. For example the inner member may be corrugated, telescoping tubes, or other designs. In some embodiments, the balloon catheter may have a radiopaque marker attached to the shaft, beneath the region.

In some embodiments, systems can employ self-expanding stents wherein a first cross-sectional area is larger than the second cross-sectional area, as indicated in FIG. 1. The cross-sectional area is proportional to the girth of the self expanding stent and is configured at the proximal and distal ends to abut the vessel wall. In a prototypical cylindrical self-expanding stent, the cross-sectional area is merely the area of a circle, for example, defined by a radius (or diameter). In some such embodiments, the first cross-sectional area is selected to allow the stent to protrude into the aneurysm sac in the expanded state. That is, the self-expanding stent at the proximal end is larger than vessel diameter. Thus, upon entering the area of the aneurysm sac, the self expanding stent begins to enter the space within the sac. This is important as it can provide a mechanism by which pressure can be reduced, thus protecting the distal lateral wall of the aneurysm. In some embodiments, the systems can employ self-expanding stents wherein the first cross-sectional area and the second cross-sectional area are approximately equal, as indicated in FIG. 2. In some such embodiments, the first cross-sectional area may or may not protrude into the aneurysm sac in the expanded state. In some embodiments, the systems can employ self-expanding stents wherein the first cross-sectional area and the second cross-sectional area are substantially circular, and wherein the first cross-sectional area has a first diameter and the second cross-sectional area has a second diameter. In some such embodiments, the systems can employ self-expanding stents wherein the narrowed portion has a greatest cross-sectional dimension less than the first diameter and the second diameter.

In some embodiments, a larger proximal end is about 1% larger than a distal end. In other embodiments, a larger proximal end is about 5% larger than a distal end. In other embodiments, a larger proximal end is about 10% larger than a distal end. In other embodiments, a larger proximal end is about 15% larger than a distal end. In other embodiments, a larger proximal end is about 20% larger than a distal end. In other embodiments, a larger proximal end is about 25% larger than a distal end. In other embodiments, a larger proximal end is in a range from about 1% to about 25% larger than a distal end, including any value therebetween and fractions thereof.

In some embodiments, some systems can employ self-expanding stents wherein the narrowed portion is circumferentially uniform, as in FIGS. 1 and 2. In some embodiments, the systems can employ self-expanding stents wherein the proximal portions 100 and 210, respectively, have a first central longitudinal axis that is substantially aligned with distal portions' 120 and 220, respectively, second central longitudinal axis, and the narrowed portions 130 and 230, respectively, have a third central longitudinal axis that is axially offset from the first and second longitudinal axes, as indicated in FIG. 3. As used herein, the "proximal portion" refers to the end of the self-expanding stent from which blood flow emanates and progresses through the lumen of the stent to the "distal portion."

In some embodiments, the systems can employ self-expanding stents wherein the narrowed portion comprises a braid density that is greater than a braid density of the proximal portion and the distal portion. In some embodiments, the systems can employ self-expanding stents wherein the narrowed portion further comprises a coating. By reducing the porosity at the narrowing, further diversion of the flow and pressure against the distal lateral wall is achieved. In some embodiments, the reduction in pressures is about 5%. In other embodiments, the reduction in pressure is about 10% and in other embodiments about 15%. In still further embodiments, the reduction in pressure is about 20%.

In some embodiments, the systems can employ self-expanding stents wherein the self-expanding stent further comprises a radiopaque marker disposed at a proximal end of the distal portion where the self-expanding stent transitions to the narrowed portion. Such radiopaque markers can be used with any of the delivery devices described above and shown in FIGS. 4-7.

Referring back to FIG. 1, in some embodiments, there is provided a self-expanding stent 100 comprising a proximal portion 110 having a first cross-sectional area in an expanded state, a distal portion 120 having a second cross-sectional area in an expanded state, a narrowed portion 130 between proximal portion 110 and the distal portion 120, narrowed portion 130 comprising a cross-sectional area when in an expanded state that is less than the first cross-sectional area and the second cross-sectional area, wherein narrowed portion 130 is configured to reduce the flow toward and pressure against a distal wall of the aneurysm by being axially disposed within the vessel substantially between a proximal edge and a distal edge of an aneurysm neck or ostium.

In some embodiments, pre-shaped self-expanding stents with narrowed portions are disposed within a vessel at the site of an aneurysm. The self-expanding stents alter the flow dynamics reducing flow and pressure at the distal lateral wall of the aneurysm. In some embodiments, any of the self expanding stents disclosed herein can be braided or cut from tube, for example. Generally, the stent may be any structure that has a porosity that is adjustable by changing an axial length of the stent. For example, the stent may be comprised of braided strands or may be comprised of a laser cut metal tube that is able to be axially shortened during and/or after diametrical expansion, with associated change in stent mesh porosity. In some embodiments, the stent may be a coil stent. Embodiments disclosed herein provide stents that are generally self-expanding.

As shown in FIG. 1, in some embodiments, the self expanding stents may have the first cross-sectional area A that is larger than the second cross-sectional area B. In some such embodiments, the self-expanding stent may protrude or at least partially extend into the aneurysm sac in the expanded state. By extending into the aneurysm sac, thrombosis may be modulated allowing more effective isolation of the aneurysm and facilitating resorption.

In some embodiments, the self-expanding stents may have a first cross-sectional area and the second cross-sectional area that are substantially circular, and, in some such embodiments, the first cross-sectional area has a first diameter and the second cross-sectional area has a second diameter. Further, in some such embodiments, the narrowed portion may have a greatest cross-sectional dimension less than the first diameter and the second diameter. As indicated above, a wider proximal diameter may allow the self-expanding stent to extend into the space of the aneurysm when deployed. In some embodiments, such configurations indicated in FIG. 1 may benefit from a pronounced reduced pressure distal to the narrowing due to the extension of the self-expanding stent into the space of the aneurysm sac.

As shown in FIG. 2, the first cross-sectional area and the second cross-sectional area may be approximately equal. Thus, self-expanding stent 200, may comprise a proximal portion 210 having a first cross-sectional area in an expanded state, a distal portion 220 having a second cross-sectional area in an expanded state, a narrowed portion 230 between proximal portion 210 and the distal portion 220, wherein the first and second cross-sectional area are approximately the same. Such uniformity in design may facilitate ease of manufacture and delivery to the aneurysm.

While embodiments shown in FIGS. 1 and 2 have narrowed portions, 130 and 230, respectively, which are substantially circumferentially uniform, FIG. 3 shows a self-expanding stent 300 in an alternate embodiment wherein the narrowed portion 330 is not circumferentially uniform. In some such embodiments, the proximal portion 310 and distal portion 320, each have respective first and second central longitudinal axes that are substantially axially aligned, and narrowed portion has a central longitudinal axis that is axially offset from the first and second longitudinal axes. In some embodiments, such designs as shown in FIG. 3, provide a narrowing while assuring stent contact with the vessel wall distal to and opposite to the aneurysm. In some such embodiments, proximal portion 310 and distal portion 320 may differ in cross-sectional area, analogous to FIG. 1. In other embodiments, the proximal portion 310 and distal portion 320 may have about the same cross-sectional area, analogous to FIG. 2.

For simplicity, the self-expanding stents in FIGS. 1-3 may be approximately circular in shape, however, as will be recognized by those skilled in the art, the geometry need not be limited to circular cross sections. For example, in some embodiments, the cross-sections may be oval or any polygonal shape.

Figure 8:
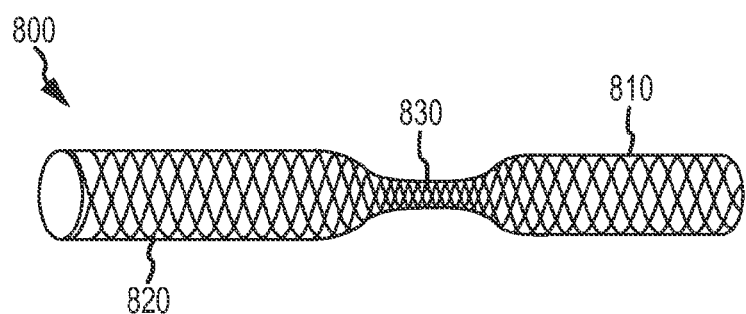
FIG. 8 shows a self-expanding stent have an increased mesh (braid) density at the narrowed portion, in accordance with some embodiments.

In some embodiments, the self-expanding stents may comprise narrowed portions comprising a braid density that is greater than a braid density of the proximal portion and the distal portion. Thus, there may be an increased mesh (e.g., braid) density at the narrowed portion, as indicated in FIG. 8. FIG. 8 shows a self-expanding stent 800 having a proximal portion 810, a distal portion 820, and a narrowed portion 830, narrowed portion 830 having an increased mesh density relative to the densities of proximal portion 810 and distal portion 820. Such changes in mesh density at narrowed portion 830 may provide further benefits in relieving the stress placed on the distal lateral wall of the aneurysm sac. In some embodiments, the increased density facilitates reduction of flow and pressure against the distal lateral wall of the aneurysm, thus reducing risk of rupture.

In some embodiments, self-expanding stents may comprise a narrowed portion comprising a coating. Such coating may perform nominally the same function as increased braid density as described above. Such coatings may comprise polymers, such as polyesters and extensible films, as known in the art. In some embodiments, the coatings can include thermoplastic or thermoset polymers, for example, an epoxy, a polyester, a vinylester, a polyetherimide, a polyetherketoneketone, a polyphthalamide, a polyetherketone, a polytheretherketone, a polyimide, a phenol-formaldehyde, and a bismaleimide. Thermosetting resins useful as coating materials can include phthalic/maelic type polyesters, vinyl esters, epoxies, phenolics, cyanates, bismaleimides, and nadic end-capped polyimides (e.g., PMR-15). Thermoplastic resins include polysulfones, polyamides, polycarbonates, polyphenylene oxides, polysulfides, polyether ether ketones, polyether sulfones, polyamide-imides, polyetherimides, polyimides, polyarylates, and liquid crystalline polyester. In some embodiments, biodegradable polymers may be employed including, without limitation, polylactic acid (PLA), polyglycolic acid (PGA), and poly(lactic-co-glycolic acid) (PGLA). Regarding the latter copolymer, one skilled in the art will recognize that any of the aforementioned polymer materials can be used in combinations of copolymer types, such as block copolymers, interpolymers, and the like. Alternatively, in some embodiments, the self-expanding stents may be manufactured with increased pore density at the narrowed portion by way of laser cut design directly from a solid shaped piece.

In some embodiments, self-expanding stents may further comprise a radiopaque marker 340, as shown in exemplary FIG. 3. Such radiopaque markers can be provided as tubular marker bands over one or more mesh strands or the like. Radiopaque markers include those disclosed, for example, in U.S. Pat. No. 8,137,376, the relevant portions of which are incorporated herein by reference. In some embodiments, the radiopaque marker can be integral with the braid via braid threads. In some embodiments radiopaque markers may comprise a coating. In some embodiments, the radiopaque marker is disposed at the distal end of the narrowed portion to facilitate alignment with the distal lateral wall of the aneurysm sac.

In some embodiments, the self-expanding stent can include markers that are disposed at a proximal end of the distal portion where the self-expanding stent transitions to the narrowed portion. In use, the radiopaque marker may be aligned with the distal lateral wall of the aneurysm, as described herein. In some embodiments, the radiopaque marker may be disposed around the entirety of the circumference of the self-expanding stent. In some embodiments, the radiopaque marker may be disposed around a portion of the circumference of the self-expanding stent. With reference to FIG. 3, in some embodiments, the radiopaque marker may be provided about the outline of the narrowed portion of the self-expanding stent.

Figure 9:
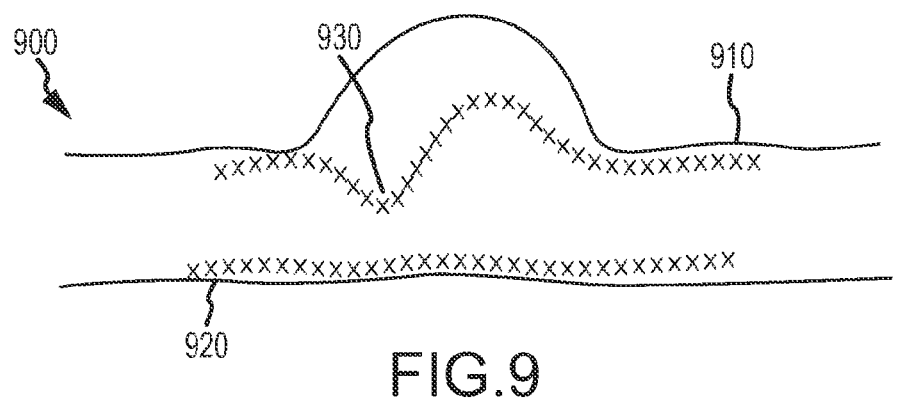
FIG. 9 shows a deployed self-expanding stent at the site of an aneurysm, in accordance with some embodiments.

In some embodiments, methods of treating an aneurysm can include positioning a self-expanding stent at an aneurysm, the self-expanding stent comprising a proximal portion having a first cross-sectional area in an expanded state, a distal portion having a second cross-sectional area in an expanded state, a narrowed portion between the proximal portion and the distal portion, the narrowed portion comprising a cross-sectional area when in an expanded state that is less than the first cross-sectional area and the second cross-sectional area, wherein the narrowed portion is configured to reduce the flow toward and pressure against a distal wall of the aneurysm by being axially disposed substantially between a proximal edge and a distal edge of an aneurysm neck or ostium, as shown in FIG. 9, and the method further comprising expanding the self-expanding stent. As shown in the figure, flow that would normally be directed through the vessel against the distal wall of the aneurysm is redirected through the stent. The reduced or narrowed portion pulls the wall of the stent away from the distal wall of the aneurysm, and the force that would be applied against the distal wall of the aneurysm is reapplied downstream where the stent is engaged against the wall of the vessel. This reduces the direct pressure against the distal wall of the aneurysm and reduces the likelihood of the aneurysm from propagating or growing.

Figure 10:
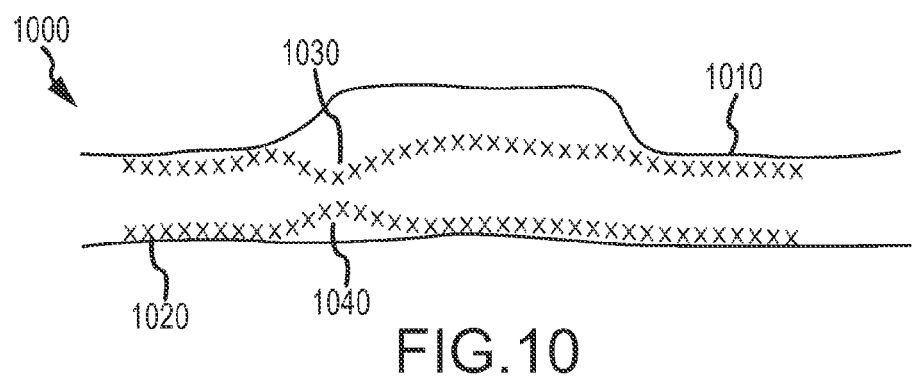
FIG. 10 show another deployed self-expanding stent at the site of an aneurysm, in accordance with some embodiments.

Methods may be performed with self-expanding stents having the first cross-sectional area is larger than the second cross-sectional area, as shown in FIG. 9. In some such embodiments, the first cross-sectional area may be selected to allow the stent to protrude into the aneurysm sac in the expanded state, as shown. In some embodiments, methods may be performed with self-expanding stents having the first cross-sectional area and the second cross-sectional area approximately equal in size, as indicated in FIG. 10. In some embodiments, with either the expanded cross-sectional area of the proximal portion or approximately equivalent cross-sectional area of the proximal portion, the portion of the self-expanding stent distal to the aneurysm may be either flush with the vessel wall, as indicated in FIG. 9 or may maintain the narrowed portion uniformity as shown in FIG. 10 as a void volume 1040. In some embodiments, it may be beneficial to assure that the stent distal to the aneurysm lays flush against the vessel to avoid thrombosis.

In some embodiments, methods employ a self-expanding stent having a narrowed portion that is circumferentially uniform, and wherein the positioning step comprises axially aligning the narrow portion along a central longitudinal axis of at least one of the proximal or distal portions. In other embodiments, the proximal, distal, and narrow portions each have respective first, second, and third central longitudinal axes, and the positioning step comprises positioning the stent such that the first and second longitudinal axes are substantially axially aligned and the third longitudinal axis is axially offset from the first and second longitudinal axes.

In some aspects, the self-expanding stent may be configured such that when deployed, the stent has a higher density (lower porosity) at the narrowed portion. Thus, methods may include the use of a self-expanding stent with a narrowed portion comprising a braid density that is greater than the braid density of the proximal portion and the distal portion. some methods employ a self-expanding stent wherein the narrowed portion further comprises a coating.

In some embodiments, methods comprise a positioning step comprising aligning a radio opaque marker, disposed at a proximal end of the distal portion on the self-expanding stent, with the distal wall of the aneurysm.

In methods, positioning may be aided by radiopaque marker for longitudinal placement, in some embodiments. In some such embodiments, placement may be determined by a fixed distance from lateral distal wall of the aneurysm. In designs with larger proximal diameter, self-extending stents may extend into space of the aneurysm. In some embodiments, where asymmetric narrowed portions are employed, such as the self-expanding stent shown in FIG. 3, both radial and longitudinal alignment may be required.

In some methods, the self-expanding stent and delivery system may manufactured to ship ready for use. The self-expanding stent delivery system may be advanced percutaneously over a guidewire to the site of an aneurysm of a blood vessel of the brain, for example. In some embodiments of stent delivery system, the radiopaque marker is attached to inner tube centrally beneath the higher density portion of the self-expanding stent and during delivery, and the radiopaque marker is positioned at the distal lateral wall of the aneurysm such that the distal end of the narrowed portion abuts the distal lateral wall of the aneurysm as shown in FIGS. 9 and 10.

When in use, the outer sheath of a typical stent delivery device may be withdrawn proximally while holding the inner tube stationary, thereby exposing the self-expanding stent. The outer sheath may be withdrawn until the distal end of outer sheath is proximal to the self-expanding stent. In some embodiments, the self-expanding stent may be partially diametrically expanded and partially axially shortened. If the physician decides to reposition the partially deployed device at this time, for example to assure the narrowed portion of the stent will be properly positioned relative to the distal lateral wall of the aneurysm neck, he/she can do so.

The apparatus and methods discussed herein are not limited to the deployment and use of an occluding device or stent within the vascular system but may include any number of further treatment applications. Other treatment sites may include areas or regions of the body such as organ bodies. Modification of each of the above-described apparatus and methods for carrying out the subject technology, and variations of aspects of the disclosure that are apparent to those of skill in the art are intended to be within the scope of the claims. Furthermore, no element, component, or method step is intended to be dedicated to the public regardless of whether the element, component, or method step is explicitly recited in the claims.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations which will be apparent to those skilled in the art may be made in the arrangement, operation and details of the method and apparatus of the subject technology disclosed herein without departing from the spirit and scope of the subject technology as defined in the appended claims. Therefore, the scope of the subject technology should be determined by the appended claims and their legal equivalents. Furthermore, no element, component or method step is intended to be dedicated to the public regardless of whether the element, component or method step is explicitly recited in the claims. Underlined and/or italicized headings and subheadings are used for convenience only, do not limit the subject technology, and are not referred to in connection with the interpretation of the description of the subject technology. In the claims and description, unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed by the claims.

What is claimed is:

1. A self-expanding braided stent comprising:
   a proximal portion formed by a plurality of helically braided filaments, wherein when the stent is in an expanded, pre-shaped state the proximal portion has a first central longitudinal axis and a first cross-sectional area;
   a distal portion formed by the plurality of helically braided filaments, wherein when the stent is in the expanded, pre-shaped state the distal portion has a second central longitudinal axis and a second cross-sectional area; and
   a narrowed portion between the proximal portion and the distal portion, the narrowed portion formed by the plurality of helically braided filaments, wherein when the stent is in the expanded, pre-shaped state the narrowed portions has a third central longitudinal axis and a third cross-sectional area that is less than the first cross-sectional area and the second cross-sectional area,
   wherein when the stent is in the expanded, pre-shaped state:
      the narrowed portion comprises a porosity defined by the plurality of helically braided filaments that is lower than a porosity of the proximal portion and a porosity of the distal portion,
      the first and the second central longitudinal axes are axially aligned and the third central longitudinal axis is axially offset from the first and the second central longitudinal axes,
      the proximal portion has a uniform diameter along a first length extending from a first end of the stent to the narrowed portion, and
      the distal portion has a uniform diameter along a second length extending from a second end of the stent to the narrowed portion.

2. The self-expanding stent of claim 1, wherein the narrowed portion of the stent is configured to reduce flow against a distal wall of an aneurysm of a body vessel.

3. The self-expanding stent of claim 1, wherein the first cross-sectional area is larger than the second cross-sectional area.

4. The self-expanding stent of claim 3, wherein the first cross-sectional area is selected to allow the stent to protrude into an aneurysm of a body vessel when the stent is expanded in the body vessel.

5. The self-expanding stent of claim 1, wherein the first cross-sectional area and the second cross-sectional area are equal.

6. The self-expanding stent of claim 1, wherein the proximal portion comprises an intermediate portion formed by the plurality of helically braided filaments, and wherein when the stent is expanded within a body vessel across an ostium of an aneurysm: (1) the intermediate portion comprises a fourth cross-sectional area greater than any other cross-sectional area of the stent outside the intermediate portion and (2) at least some of the intermediate portion does not contact the body vessel.

7. The self-expanding stent of claim 1, wherein the narrowed portion further comprises a coating.

8. The self-expanding stent of claim 1, further comprising a radio opaque marker disposed at a proximal end of the distal portion where the self-expanding stent transitions to the narrowed portion.

9. The self-expanding stent of claim 1, wherein the first cross-sectional area and the second cross-sectional area are circular, and wherein the first cross-sectional area has a first diameter and the second cross-sectional area has a second diameter.

10. The self-expanding stent of claim 9, wherein the narrowed portion has a greatest cross-sectional dimension less than the first diameter and the second diameter.

11. The self-expanding stent of claim 1, wherein the narrowed portion is configured such that when the stent is expanded within a body vessel across an ostium of an aneurysm, at least some of the narrowed portion does not contact the body vessel.

12. A system comprising:
a self-expanding stent comprising:
  a proximal portion, wherein when the stent is in an expanded, pre-shaped state the proximal portion has a first central longitudinal axis and a first cross-sectional area;
  a distal portion, wherein when the stent is in the expanded, pre-shaped state the distal portion has a second central longitudinal axis and a second cross-sectional area; and
  a narrowed portion between the proximal portion and the distal portion, wherein when the stent is in the expanded, pre-shaped state the narrowed portion has a third central longitudinal axis and a third cross-sectional area that is less than the first cross-sectional area and the second cross-sectional area,
wherein the stent is formed of a plurality of braided filaments extending along an entire length of the stent,
wherein when the stent is in the expanded, pre-shaped state:
  the narrowed portion comprises a porosity defined by the braided filaments that is lower than a porosity of the proximal portion and a porosity of the distal portion,
  the first and the second central longitudinal axes are axially aligned and the third central longitudinal axis is axially offset from the first and the second central longitudinal axes,
  the proximal portion has a uniform diameter along a first length extending from a first end of the stent to the narrowed portion, and
  the distal portion has a uniform diameter along a second length extending from a second end of the stent to the narrowed portion; and
a stent delivery device configured to position and release the self-expanding stent.

13. The system of claim 12, wherein the first cross-sectional area is larger than the second cross-sectional area.

14. The system of claim 13, wherein the first cross-sectional area is selected to allow the stent to protrude into an aneurysm of a body vessel when the stent is expanded in the body vessel.

15. The system of claim 12, wherein the first cross-sectional area and the second cross-sectional area are equal.

16. The system of claim 12, wherein the proximal portion comprises an intermediate portion, and wherein when the stent is expanded within a body vessel across an ostium of an aneurysm: (1) the intermediate portion comprises a fourth cross-sectional area greater than any other cross-sectional area of the stent outside the intermediate portion and (2) at least some of the intermediate portion does not contact the body vessel.

17. The system of claim 12, wherein the narrowed portion further comprises a coating.

18. The system of claim 12, wherein the self-expanding stent further comprises a radio opaque marker disposed at a proximal end of the distal portion where the self-expanding stent transitions to the narrowed portion.

19. The system of claim 12, wherein the first cross-sectional area and the second cross-sectional area are circular, and wherein the first cross-sectional area has a first diameter and the second cross-sectional area has a second diameter.

20. The system of claim 19, wherein the narrowed portion has a greatest cross-sectional dimension less than the first diameter and the second diameter.

21. The system of claim 12, wherein the narrowed portion is configured such that when the stent is expanded within a body vessel across an ostium of an aneurysm, at least some of the narrowed portion does not contact the body vessel.

* * * * *